US012071622B2

(12) United States Patent
Lulla et al.

(10) Patent No.: US 12,071,622 B2
(45) Date of Patent: *Aug. 27, 2024

(54) miR-3132 UPREGULATION OF THE TRAIL PATHWAY AND APOPTOTIC ACTIVITY IN CANCER CELLS

(71) Applicant: Institute For Cancer Research, Philadelphia, PA (US)

(72) Inventors: Amriti R. Lulla, Philadelphia, PA (US); Wafik S. El-Deiry, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,881

(22) Filed: Jan. 4, 2023

(65) Prior Publication Data

US 2023/0340478 A1    Oct. 26, 2023

Related U.S. Application Data

(63) Continuation of application No. 16/980,005, filed as application No. PCT/US2019/021541 on Mar. 11, 2019, now Pat. No. 11,578,324.

(60) Provisional application No. 62/642,117, filed on Mar. 13, 2018.

(51) Int. Cl.
| | |
|---|---|
| C12N 15/113 | (2010.01) |
| A61K 31/7105 | (2006.01) |
| A61K 39/395 | (2006.01) |
| C07K 16/28 | (2006.01) |
| C12Q 1/6886 | (2018.01) |

(52) U.S. Cl.
CPC ........ *C12N 15/113* (2013.01); *A61K 31/7105* (2013.01); *A61K 39/39533* (2013.01); *C07K 16/2875* (2013.01); *C12Q 1/6886* (2013.01); C07K 2317/76 (2013.01); C12N 2310/141 (2013.01); C12N 2320/31 (2013.01); C12Q 2600/106 (2013.01); C12Q 2600/158 (2013.01); C12Q 2600/178 (2013.01)

(58) Field of Classification Search
CPC .................................................. C12N 15/113
USPC ...................................................... 424/133.1
See application file for complete search history.

(56) References Cited

U.S. PATENT DOCUMENTS

| 11,578,324 B2 * | 2/2023 | Lulla ................ A61K 33/243 |
| 2009/0004145 A1 | 1/2009 | Ramesh |
| 2014/0322354 A1 | 10/2014 | Goel et al. |

FOREIGN PATENT DOCUMENTS

WO         2014047546         3/2014

OTHER PUBLICATIONS

Lulla, "miRNAs as Therapeutics to Target Cell Cycle Progression and Promote Cell Death In Cancer Cells", Dissertation, Penn State University, 2018, http://etda.libraries.psu.edu/catalog/15216arl189.
Stark et al., "Characterization of the Melanoma miRNAome by Deep Sequencing", PLoS One, 2010, 5(3), pp. 1-9.
Blanarova et al., "Cisplatin and a potent platinum (IV) complex-mediated enhancement of TRAIL-induced cancer cells killing is associated with modulation of upstream events in the extrinsic apoptotic pathway", Carcinogenesis, 2011, 32(1), pp. 42-51.
Jung et al., "Predicitve microRNAs for lymph node metastasis in endoscopically resectable submucosal colorectal cancer", Oncotarget, 2016, 7(22), pp. 32902-32915.
Takahashi et al., "p53: A Frequent Target for Genetic Abnormalities in Lung Cancer", Science, 1989, 246(4929), pp. 491-494.
Li et al., "p53 mutations in colorectal cancer-molecular pathogenesis and pharmacological reactivation", World J Gastro, 2015, 21(1), pp. 64-93.
Wang et al., "MicroRNA-494 Targeting Both Proapoptotic and Antiapoptotic Proteins Protects Against Ischemia/Reperfusion-Induced Cardiac Injury", Circulation, 2010, 122(13), pp. 1308-1318.
Wang et al., "5-Fluorouracil preferentially sensitizes mutant KRAS non-small cell lung carcinoma cells to TRAIL-induced apoptosis", Molecular Oncology, 2015, 9, pp. 1815-1824.
Allen et al., "Regulation of the human TRAIL gene", Cancer Biol Ther, 2012, 13, pp. 1143-1151.
Lim et al., "Targeting TRAIL in the treatment of cancer: new developments", Expert Opin Ther Targets, 2015, 19, pp. 1171-1185.
Friedman et al., "Most mammalian mRNAs are conserved targets of microRNAs", Genome Res, 2009, 19, pp. 92-105.
Ameres et al., "Diversifying microRNA sequence and function", Nat Rev Mol Cell Biol, 2013, 14, pp. 475-488.
Oom et al., "MicroRNAs: Emerging Novel Targets of Cancer Therapies", Biomed Res Int, 2014, 2014, 959461, pp. 1-14.
Iorio et al., "Causes and Consequences of microRNA Dysregulation", Cancer J, 2012, 18, pp. 215-222.
Suzuki et al., "DNA methylation and microRNA dysregulation in cancer", Mol Oncol, 2012, 6, pp. 567-578.
Iorio et al., "MicroRNA dysregulation in cancer: diagnostics, monitoring and therapeutics. A comprehensive review", EMBO Mol Med, 2012, 4, pp. 143-159.
Zhu et al., "The Synergistic Effects of Low Dose Fluorouracil and TRAIL on TRAIL-Resistant Human Gastric Adenocarcinoma AGS Cells", Biomed Res Int, 2013, 2013, 293874, pp.

* cited by examiner

*Primary Examiner* — Sean E Aeder
(74) *Attorney, Agent, or Firm* — Armstrong Teasdale LLP

(57) ABSTRACT

The present disclosure provides compositions comprising miR-3132 and one or more pharmaceutical agents that upregulate TNF-related apoptosis-inducing ligand (TRAIL) or activate TRAIL signaling pathway, and methods for treating a cancer comprising administering miR-3132, or a composition comprising miR-3132 and one or more pharmaceutical agents that upregulate TRAIL or activate TRAIL signaling pathway, to a subject.

11 Claims, 26 Drawing Sheets

Specification includes a Sequence Listing.

B.

C.

D.

A.

| No | Ingenuity Canonical Pathways | -log(p-value) | Ratio | Molecules |
|---|---|---|---|---|
| 1 | Interferon Signaling | 7.81 | 0.222 | IFIT3, IFIT1, OAS1, MX1, IFI6, STAT2, IRF9, STAT1 |
| 2 | p38 MAPK Signaling | 3.9 | 0.0696 | PLA2G4A, IL18, DDIT3, HIST1H3C, TGFB2, MKNK2, STAT1, H |
| 3 | Death Receptor Signaling | 3.74 | 0.0769 | MAP3K14, TNKS, TNFSF10, TNFSF15, BIRC3, PARP9, HSP |
| 4 | Pattern Recognition Receptors in Recognition of Bacteria and Viruses | 2.79 | 0.0534 | CXCL8, IL18, OAS1, TLR6, DDX58, TGFB2, OAS3 |
| 5 | Toll-like Receptor Signaling | 1.79 | 0.0533 | MAP3K14, IL18, TLR6, UBC |
| 6 | Role of JAK1, JAK2 and TYK2 in Interferon Signaling | 1.42 | 0.0833 | STAT2, STAT1 |
| 7 | Colorectal Cancer Metastasis Signaling | 0.686 | 0.0207 | MMP7, TLR6, TGFB2, PTGS2, STAT1 |
| 8 | Retinoic acid Mediated Apoptosis Signaling | 2.14 | 0.0678 | TNKS, IFNE, TNFSF10, PARP9 |
| 9 | Activation of IRF by Cytosolic Pattern Recognition Receptors | 2.09 | 0.0656 | DDX58, STAT2, IRF9, STAT1 |
| 10 | TREM1 Signaling | 1.89 | 0.0571 | CXCL8, IL18, ICAM1, TLR6 |

| No | Ingenuity Canonical Pathways | -log(p-value) | Ratio | Molecules |
|---|---|---|---|---|
| 11 | NF-κB Signaling | 0.728 | 0.0231 | MAP3K14, IL18, TLR6, MAP3K8 |
| 12 | Production of Nitric Oxide and ROS in Macrophages | 0.628 | 0.0209 | MAP3K14, MAP3K8, STAT1, CLU |
| 13 | Granulocyte Adhesion and Diapedesis | 2.29 | 0.0435 | CXCL8, IL18, MMP7, ICAM1, CLDN1, CCL20, HSPB1 |
| 14 | Wnt/β-catenin Signaling | 1.16 | 0.0296 | MMP7, TGFB2, GNAQ, DKK1, UBC |
| 15 | IL-6 Signaling | 1.07 | 0.0312 | CXCL8, MAP3K14, IL18, HSPB1 |
| 16 | HMGB1 Signaling | 1.04 | 0.0305 | CXCL8, IL18, ICAM1, TGFB2 |
| 17 | Leukocyte Extravasation Signaling | 0.898 | 0.0245 | TIMP4, MMP7, ICAM1, CLDN1, TIMP2 |
| 18 | Dendritic Cell Maturation | 1.08 | 0.0291 | MAP3K14, IL18, ICAM1, STAT2, STAT1 |
| 19 | Endothelin-1 Signaling | 0.659 | 0.0216 | PLA2G4A, EDN1, GNAQ, PTGS2 |
| 20 | B Cell Receptor Signaling | 0.654 | 0.0215 | MAP3K14, LYN, MAP3K8, PIK3AP1 |

| Upstream Regulator | Predicted State | Activation z-score | p-value of overl. |
|---|---|---|---|
| IRF7 | Activated | 4.554 | 6.45E-19 |
| IRF3 | Activated | 3.801 | 6.29E-17 |
| IRF1 | Activated | 3.752 | 8.59E-17 |
| STAT1 | Activated | 4.448 | 1.11E-15 |
| STAT2 | Activated | 2.57 | 1.22E-13 |
| TP53 | Activated | 2.328 | 6.83E-12 |
| IRF9 | Activated | 2.4 | 6.63E-11 |
| NFKB1 | Activated | 3.066 | 1.48E-09 |
| IRF5 | Activated | 3.094 | 2.18E-09 |
| MYC | | -1.487 | 2.47E-08 |
| IFI16 | Activated | 2.583 | 0.0000218 |
| YAP1 | Activated | 2.421 | 0.00185 |
| FOXO1 | Activated | 2.376 | 0.0138 |

Figure 8

| No | GSEA Set name | Biological features |
|---|---|---|
| 1 | BROWNE_INTERFERON_RESPONSIVE_GENES | Genes upregulated in response to IFN α |
| 2 | REACTOME_INTERFERON_SIGNALING | Genes involved in Interferon Signaling |
| 3 | GO_RESPONSE_TO_TYPE_I_INTERFERON | Response to Type I interferons include interferon-α, β, δ, ε, κ, τ, and ω gene families |
| 4 | GO_CELL_DEATH | Biological process that results in permanent cessation of all vital functions of a cell |
| 5 | GO_REGULATION_OF_CELL_DEATH | Any process that modulates the rate or frequency of cell death |
| 6 | REACTOME_CYTOKINE_SIGNALING_IN_IMMUNE_SYSTEM | Genes involved in Cytokine Signaling in Immune system |
| 7 | GO_RESPONSE_TO_CYTOKINE | Process that results in a change in state/activity of a cell as a result of a cytokine stimulus |
| 8 | REACTOME_IMMUNE_SYSTEM | Genes involved in Immune System |
| 9 | GO_IMMUNE_SYSTEM_PROCESS | Any process involved in the development or functioning of the immune system |
| 10 | GO_DEFENSE_RESPONSE | Triggered in response to the presence of a foreign body or the occurrence of an injury |
| 11 | GO_DEFENCE_RESPONSE_TO_OTHER_ORGANISM | Presence of another organism that act to protect the cell or organism from damage |
| 12 | GO_REGULATION_OF_RESPONSE_TO_STRESS | Any process that modulates the frequency, rate or extent of a response to stress |

*= Enrichment Score; **= Normalized Enrichment score

Figure 9

| No | GSEA Set name | ES* | NES** | Nominal p-value | FDR Q value |
|---|---|---|---|---|---|
| 1 | BROWNE_INTERFERON_RESPONSIVE_GENES | 0.58723 | 2.395106 | 0.00 | 8.52E-04 |
| 2 | REACTOME_INTERFERON_SIGNALING | 0.62751 | 2.65369 | 0.00 | 2.45E-04 |
| 3 | GO_RESPONSE_TO_TYPE_I_INTERFERON | 0.621962 | 2.473484 | 0.00 | 9.17E-04 |
| 4 | GO_CELL_DEATH | 0.694338 | 2.793401 | 0.00 | 0.00 |
| 5 | GO_REGULATION_OF_CELL_DEATH | 0.491399 | 2.548584 | 0.00 | 1.64E-04 |
| 6 | REACTOME_CYTOKINE_SIGNALING_IN_IMMUNE_SYSTEM | 0.572537 | 2.616904 | 0.00 | 2.71E-04 |
| 7 | GO_RESPONSE_TO_CYTOKINE | 0.467387 | 2.443729 | 0.00 | 8.47E-04 |
| 8 | REACTOME_IMMUNE_SYSTEM | 0.486213 | 2.403868 | 0.00 | 7.23E-04 |
| 9 | GO_IMMUNE_SYSTEM_PROCESS | 0.418176 | 2.606087 | 0.00 | 0.00 |
| 10 | GO_DEFENSE_RESPONSE | 0.492173 | 2.863446 | 0.00 | 0.00 |
| 11 | GO_DEFENCE_RESPONSE_TO_OTHER_ORGANISM | 0.590315 | 2.627057 | 0.00 | 0.00 |
| 12 | GO_REGULATION_OF_RESPONSE_TO_STRESS | 0.463608 | 2.434166 | 0.00 | 8.73E-04 |

*= Enrichment Score; **= Normalized Enrichment score

Figure 9 (cont.)

SEQUENCE LISTING

```
Sequence total quantity: 2
SEQ ID NO: 1              moltype = RNA   length = 75
FEATURE                   Location/Qualifiers
misc_feature              1..75
                          note = miR-3132
source                    1..75
                          mol_type = other RNA
                          organism = synthetic construct
SEQUENCE: 1
ggtgggatgg gtagagaagg agctcagagg acggtgcgcc ttgtttccct tgagccctcc    60
ctctctcatc ccacc                                                    75

SEQ ID NO: 2              moltype = RNA   length = 24
FEATURE                   Location/Qualifiers
misc_feature              1..24
                          note = miR-3132
source                    1..24
                          mol_type = other RNA
                          organism = synthetic construct
SEQUENCE: 2
tgggtagaga aggagctcag agga                                          24
```

miR-3132 UPREGULATION OF THE TRAIL PATHWAY AND APOPTOTIC ACTIVITY IN CANCER CELLS

REFERENCE TO SEQUENCE LISTING

This application includes a Sequence Listing filed electronically as an XML file named 853003342SEQ, created on May 22, 2023, with a size of 4 kilobytes. The Sequence Listing is incorporated herein by reference.

FIELD

The present disclosure is directed, in part, to compositions comprising miR-3132 and one or more pharmaceutical agents that upregulate TNF-related apoptosis-inducing ligand (TRAIL) or activate TRAIL signaling pathway, and methods for treating a cancer comprising administering miR-3132 to a subject.

BACKGROUND

The tumor necrosis factor (TNF) superfamily member, TNF-related apoptosis-inducing ligand (TRAIL/Apo2L), is an important pro-apoptotic effector. TRAIL induces rapid apoptosis through binding to death receptors DR4 or DR5 expressed on the surface of cells. It is involved in immune surveillance, killing both tumor cells and cells infected with bacteria and viruses. Its quick and potent apoptotic properties keep the TRAIL gene under the tight regulation by transcriptional factors such as FOXO3a, p53, AP-1, CEBP, NFAT, GATA Stat-1, IRF-1, GSP1, GSP2, and GSP4. Following activation of an immune response, interferon signaling elements, particularly IFNα, IFNβ, IFNγ, mediate Stat-1 signaling and toll-like receptors (TLRs) (TLR3, TLR7 and TL8) control TRAIL upregulation. These pathways mediate TRAIL upregulation in immune cells including natural killer cells, macrophages, dendritic cells and cytotoxic T cells. Thus, TRAIL upregulation is highly regulated event (Allen et al., Cancer Biol. Ther., 2012, 13, 1143-51; and Lim et al., Expert Opin. Ther. Targets, 2015, 19, 1171-85).

There is significant interest in the regulation of the TRAIL gene because of its unique ability to induce apoptosis in cancer cells while sparing normal and untransformed cells. This selective antitumor potential of the TRAIL pathway has been harnessed by development of different therapeutic approaches including recombinant (rh)TRAIL and TRAIL-receptor agonist antibodies such as mapatumumab and lexatumumab. Many TRAIL-based therapies have proven successful in preclinical studies and safe in early phase clinical trials. Clinical trial results revealed several limitations of rhTRAIL and TRAIL receptor agonists with serum half-life, hepatotoxicity, stability, tumor-specific cytotoxicity and biodistribution being the most evident (Allen et al., Cancer Biol. Ther., 2012, 13, 1143-51; and Lim et al., Expert Opin. Ther. Targets, 2015, 19, 1171-85). Hence, there is still an unmet clinical need for TRAIL-based anti-tumor agents with increased efficacy and safety.

miRNAs are generally 18-22 nucleotide small non-coding RNAs that can inhibit translation and/or affect mRNA stability by binding to the 3' untranslated region (UTR) of target genes (Friedman et al., Genome Res., 2009, 19, 92-105; and Ameres et al., Nat. Rev. Mol. Cell. Biol., 2013, 14, 475-88). Studies in different tumor models have shown that miRNAs can either be oncogenic, as in the case of miR-155, miR-21 and the miR17~92 cluster, or tumor suppressive (miR-34a, let-7 family and miR-143) (Oom et al., Biomed. Res. Int., 2014, 2014, 959461; and Iorio et al., Cancer J., 2012, 18, 215-22). Tumor suppressive miRNAs are dysregulated in cancer cells through multiple mechanisms including methylation of promoter sites (Suzuki et al., Mol. Oncol., 2012, 6, 567-78), deletion, or loss of expression (Iorio et al., Cancer J., 2012, 18, 215-22; and Iorio et al., EMBO Mol. Med., 2012, 4, 143-59). Re-introduction of tumor suppressive miRNAs known as "miRNA mimics" has become an attractive therapeutic strategy. Many such miRNA mimics are currently in clinical or pre-clinical development for cancer (Rupaimoole et al., Nat. Rev. Drug Discov., 2017, 16, 203-222).

SUMMARY

The present disclosure provides pharmaceutical compositions comprising a nucleic acid molecule consisting of up to about 90 nucleobases comprising a nucleotide sequence that is at least about 80% identical to miR-3132, and a pharmaceutical agent that upregulates TNF-related apoptosis-inducing ligand (TRAIL) or activates TRAIL signaling pathway.

The present disclosure also provides methods for treating a cancer comprising administering to a subject in need thereof a nucleic acid molecule consisting of up to about 90 nucleobases comprising a nucleotide sequence that is at least about 80% identical to miR-3132.

The present disclosure also provides methods of determining whether a subject having cancer is a candidate for miR-3132 treatment, comprising: measuring the amount of miR-3132 in a cancer cell from the subject; wherein if the amount of miR-3132 in the cancer cell from the subject is lower than a threshold amount of miR-3132, then the subject is a candidate for miR-3132 treatment; and wherein if the amount of miR-3132 in the cancer cell from the subject is equal to or greater than a threshold amount of miR-3132, then the subject is not a candidate for miR-3132 treatment.

These and other embodiments of the present disclosure will become apparent in conjunction with the figures, description and claims that follow.

BRIEF DESCRIPTION OF THE DRAWINGS

FIG. 8 shows a list of top activated transcriptional regulators associated with IFN response and the corresponding genes from the microarray altered.

FIG. 9 shows a representative GSEA analysis indicating list of gene sets overlapping with gene signature observed with miR-3132 microarray data.

DESCRIPTION OF EMBODIMENTS

Figure 1:
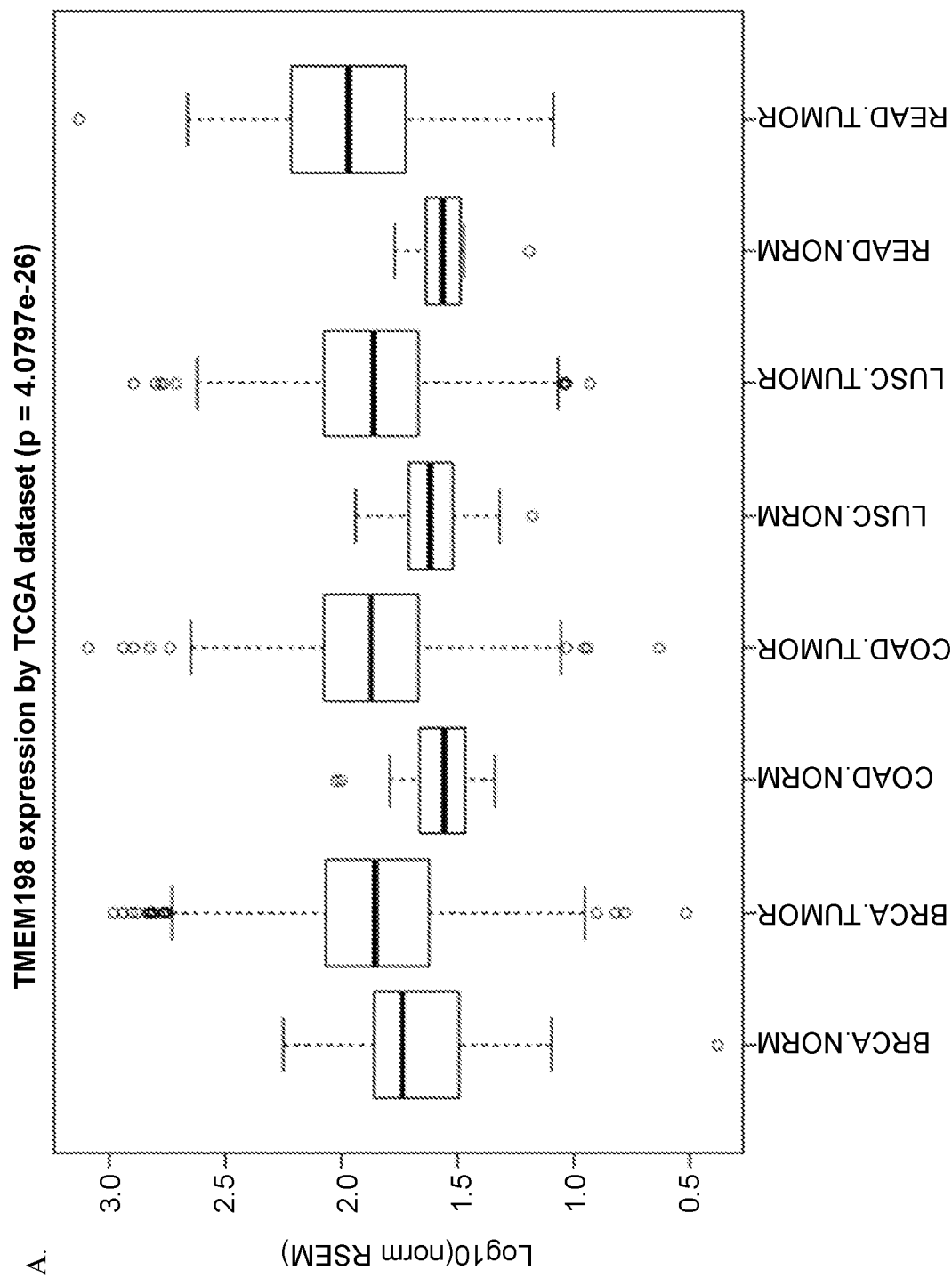
FIG. 1 (Panels A and B) shows miR-3132 expression is lost in cancer cell lines.
Figure 1:
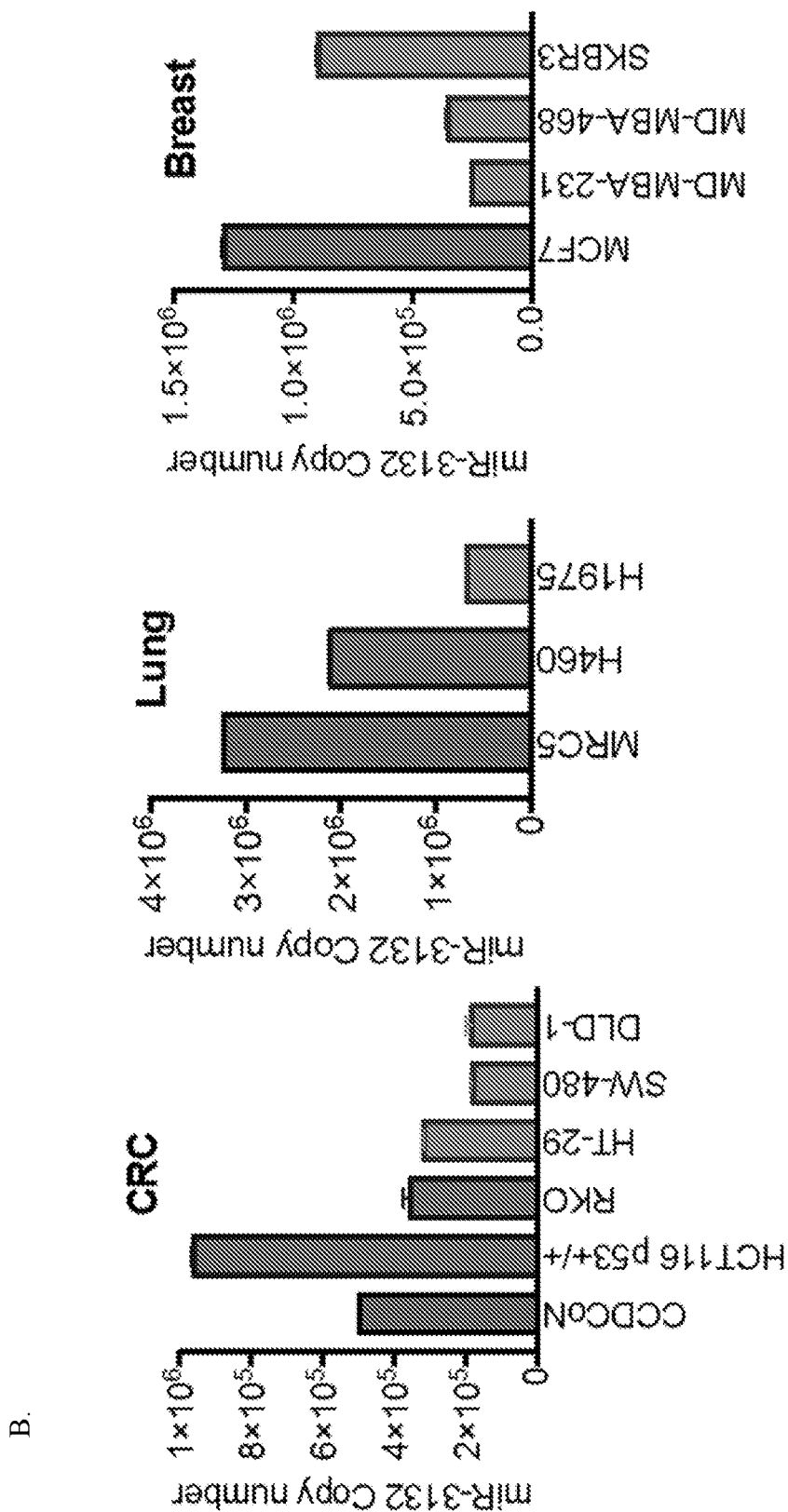

The terminology used herein is for the purpose of describing particular embodiments only and is not intended to be limiting.

Provided herein is a pre-clinical rationale for novel miRNA therapeutic, miR-3132, that has anti-proliferative and pro-apoptotic effects in a broad panel of cancer cell lines. Notably, miR-3132 induced surface TRAIL and subsequent TRAIL-dependent apoptosis in a broad range of cancer lines. Treating cells with TRAIL sequestering antibody RIK2 completely blocked miR-3132 induced apoptosis in cancer cells. The present disclosure provides the first evidence of a miRNA upregulating surface TRAIL and inducing TRAIL-dependent cell death. To gain insight into the putative mechanisms of miR-3132's pro-apoptotic effects, gene expression profiling following treatment with miR-3132 was performed. Microarray data analysis indicates that miR-3132 upregulates interferon type I signaling. It is possible that this is the upstream mechanism that explains the observed TRAIL and apoptosis induction in cancer cells. The miR-3132 induced IFN and TRAIL upregulation may be a consequence of direct binding of miR-3132 to TLRs (likely, TLR6). TLR signaling is a well characterized mechanism of IFN signaling stimulation and TLRs are well characterized dsDNA/RNA and ssRNA sensors. Recent reports suggest that miRNAs could be ligands for TLRs and induce downstream immune pathways and IFN signaling and that these binding properties are miRNA-specific.

Unless defined otherwise, all technical and scientific terms used herein have the same meaning as is commonly understood by one of skill in the arts to which the claimed subject matter.

As used herein, the singular forms "a," "an" and "the" include plural referents unless the context clearly dictates otherwise.

As used herein, "subject" means a human or non-human animal selected for diagnosis, treatment, and/or therapy.

As used herein, "in need thereof" means a subject identified as in need of a therapy or treatment. In some embodiments, a subject has a tumor or cancer. In such embodiments, a subject has one or more clinical indications of a tumor or cancer, or is at risk for developing a tumor or cancer.

As used herein, "administering" means providing a pharmaceutical agent or composition to a subject, and includes, but is not limited to, administering by a medical professional and self-administering.

As used herein, "parenteral administration," means administration through injection or infusion. Parenteral administration includes, but is not limited to, subcutaneous administration, intravenous administration, intraperitoneal administration, or intramuscular administration.

As used herein, "subcutaneous administration" means administration just below the skin.

As used herein, "intravenous administration" means administration into a vein.

As used herein, "intratumoral administration" means administration within a tumor.

As used herein, "intraperitoneal administration" means administration into the peritoneum (i.e., body cavity).

As used herein, "intramuscular administration" means administration into a muscle.

As used herein, "duration" means the period of time during which an activity or event continues. In some embodiments, the duration of treatment is the period of time during which one or more doses of a pharmaceutical agent or pharmaceutical composition are administered.

As used herein, "therapy" and/or "treatment" means the application of one or more specific procedures used for the cure or amelioration of a disease. In some embodiments, the specific procedure is the administration of one or more pharmaceutical agents.

As used herein, "amelioration" means a lessening of severity of at least one indicator of a condition or disease. In some embodiments, amelioration includes a delay or slowing in the progression of one or more indicators of a condition or disease. The severity of indicators may be determined by subjective or objective measures which are known to those skilled in the art.

As used herein, "prevention" refers to delaying or forestalling the onset or development or progression of a condition or disease for a period of time, including weeks, months, or years.

As used herein, "therapeutic agent" means a pharmaceutical agent used for the cure, amelioration or prevention of a disease.

As used herein, "chemotherapeutic agent" means a pharmaceutical agent used to treat cancer.

As used herein, "chemotherapy" means treatment of a subject with one or more pharmaceutical agents that kills cancer cells and/or slows the growth of cancer cells.

As used herein, "dose" means a specific quantity of a pharmaceutical agent provided in a single administration. A dose may be administered in two or more boluses, tablets, or injections. In some embodiments, a dose may be administered in two or more injections to minimize injection site reaction in an individual.

As used herein, "dosage unit" means a form in which a pharmaceutical agent is provided. In some embodiments, a dosage unit is a vial containing lyophilized nucleic acid molecule(s). In some embodiments, a dosage unit is a vial containing reconstituted nucleic acid molecule(s).

As used herein, "therapeutically effective amount" refers to an amount of a pharmaceutical agent that provides a therapeutic benefit to an animal.

As used herein, "pharmaceutical composition" means a mixture of substances suitable for administering to a subject that includes a pharmaceutical agent. For example, a pharmaceutical composition may comprise a nucleic acid molecule and a sterile aqueous solution.

As used herein, "pharmaceutical agent" means a substance that provides a therapeutic effect when administered to a subject.

As used herein, "overall survival time" means the time period for which a subject survives after diagnosis of or treatment for a disease.

As used herein, "acceptable safety profile" means a pattern of side effects that is within clinically acceptable limits.

As used herein, "side effect" means a physiological response attributable to a treatment other than desired effects. In some embodiments, side effects include, without limitation, injection site reactions, renal function abnormalities, liver toxicity, renal toxicity, central nervous system abnormalities, and myopathies. Such side effects may be detected directly or indirectly.

As used herein, "injection site reaction" means inflammation or abnormal redness of skin at a site of injection in an individual.

As used herein, "targeting" means the process of design and selection of nucleobase sequence that will hybridize to a target nucleic acid and induce a desired effect.

As used herein, "targeted to" means having a nucleobase sequence that will allow hybridization to a target nucleic acid to induce a desired effect.

As used herein, "expression" means any functions and steps by which a gene's coded information is converted into structures present and operating in a cell.

As used herein, "nucleobase sequence" means the order of contiguous nucleobases, in a 5' to 3' orientation, independent of any sugar, linkage, and/or nucleobase modification.

As used herein, "contiguous nucleobases" means nucleobases immediately adjacent to each other in a nucleic acid molecule.

As used herein, "percent identity" means the number of nucleobases in first nucleic acid molecule that are identical to nucleobases at corresponding positions in a second nucleic acid molecule, divided by the total number of nucleobases in the first nucleic acid molecule. Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, "hybridize" means the annealing of complementary nucleic acid molecules that occurs through nucleobase complementarity.

As used herein, "mismatch" means a nucleobase of a first nucleic acid molecule that is not capable of pairing with a nucleobase at a corresponding position of a second nucleic acid molecule.

As used herein, "identical" means having the same nucleobase sequence.

As used herein, "miR-3132" means the nucleic acid molecule having the nucleobase sequence set forth in SEQ ID NO:1 or SEQ ID NO:2.

As used herein, "oligonucleotide" means a polymer of linked nucleosides, each of which can be modified or unmodified, independent from one another.

As used herein, "naturally occurring internucleoside linkage" means a 3' to 5' phosphodiester linkage between nucleosides.

As used herein, "natural sugar" means a sugar found in DNA (2'-H) or RNA (2'-OH).

As used herein, "natural nucleobase" means a nucleobase that is unmodified relative to its naturally occurring "internucleoside linkage" means a covalent linkage between adjacent nucleosides.

As used herein, "linked nucleosides" means nucleosides joined by a covalent linkage.

As used herein, "nucleobase" means a heterocyclic moiety capable of non-covalently pairing with another nucleobase.

As used herein, "nucleoside" means a nucleobase linked to a sugar.

As used herein, "nucleotide" means a nucleoside having a phosphate group covalently linked to the sugar portion of a nucleoside.

As used herein, "modified nucleic acid molecule" means a nucleic acid molecule having one or more modifications relative to a naturally occurring terminus, sugar, nucleobase, and/or internucleoside linkage.

As used herein, "modified internucleoside linkage" means any change from a naturally occurring internucleoside linkage.

As used herein, "phosphorothioate internucleoside linkage" means a linkage between nucleosides where one of the non-bridging atoms is a sulfur atom.

As used herein, "modified sugar" means substitution and/or any change from a natural sugar.

As used herein, "modified nucleobase" means any substitution and/or change from a natural nucleobase.

As used herein, "5-methylcytosine" means a cytosine modified with a methyl group attached to the 5' position.

As used herein, "2'-O-methyl sugar" or "2'-O-Me sugar" means a sugar having an O-methyl modification at the 2' position.

As used herein, "2'-O-methoxyethyl sugar" or "2'-MOE sugar" means a sugar having a O-methoxyethyl modification at the 2' position.

As used herein, "2'-O-fluoro" or "2'-F" means a sugar having a fluoro modification of the 2' position.

As used herein, "bicyclic sugar moiety" means a sugar modified by the bridging of two non-geminal ring atoms.

As used herein, "2'-O-methoxyethyl nucleoside" means a 2'-modified nucleoside having a 2'-O-methoxyethyl sugar modification.

As used herein, "2'-fluoro nucleoside" means a 2'-modified nucleoside having a 2'-fluoro sugar modification.

As used herein, "2'-O-methyl" nucleoside means a 2'-modified nucleoside having a 2'-O-methyl sugar modification.

As used herein, "bicyclic nucleoside" means a 2'-modified nucleoside having a bicyclic sugar moiety.

As used herein, "motif" means a pattern of modified and/or unmodified nucleobases, sugars, and/or internucleoside linkages in a nucleic acid molecule.

As used herein, a "fully modified nucleic acid molecule" means each nucleobase, each sugar, and/or each internucleoside linkage within a nucleic acid molecule is modified.

As used herein, a "uniformly modified nucleic acid molecule" means each nucleobase, each sugar, and/or each internucleoside linkage within a nucleic acid molecule has the same modification throughout the modified nucleic acid molecule.

As used herein, a "stabilizing modification" means a modification to a nucleoside that provides enhanced stability to a modified nucleic acid molecule, in the presence of nucleases, relative to that provided by 2'-deoxynucleosides linked by phosphodiester internucleoside linkages. For example, in some embodiments, a stabilizing modification is a stabilizing nucleoside modification. In some embodiments, a stabilizing modification is a internucleoside linkage modification.

As used herein, a "stabilizing nucleoside" means a nucleoside modified to provide enhanced nuclease stability to a nucleic acid molecule, relative to that provided by a 2'-deoxynucleoside. In one embodiment, a stabilizing nucleoside is a 2'-modified nucleoside.

As used herein, a "stabilizing internucleoside linkage" means an internucleoside linkage that provides enhanced nuclease stability to a nucleic acid molecule relative to that provided by a phosphodiester internucleoside linkage. In one embodiment, a stabilizing internucleoside linkage is a phosphorothioate internucleoside linkage.

The present disclosure provides pharmaceutical compositions comprising: a nucleic acid molecule consisting of up to about 90 nucleobases comprising a nucleotide sequence that is at least about 80% identical to GGUGGGAUGG- GUAGAGAAGGAGCUCAGAGGA CGGUGCGCCUU-
GUUUCCCUUGAGCCCUCCCUCUCUCAUCCCACC
(SEQ ID NO:1) or UGGGUAGAGAAGGAG-
CUCAGAGGA (SEQ ID NO:2); and at least one pharmaceutical agent that upregulates TNF-related apoptosis-inducing ligand (TRAIL) or activates TRAIL signaling pathway.

In some embodiments, the nucleic acid molecule consists of up to about 90 nucleobases and comprises a nucleotide sequence that is at least about 80% identical to SEQ ID NO: 1. In some embodiments, the nucleic acid molecule consists of up to about 85 nucleobases, up to about 80 nucleobases, or up to 75 nucleobases. In some embodiments, the nucleic acid molecule consists of 75 to 90 linked nucleobases, of 75 to 85 linked nucleobases, or 75 to 80 linked nucleobases. In some embodiments, the nucleic acid molecule comprises a nucleotide sequence that is at least about 80%, at least about 85%, at least about 90%, at least about 95%, at least about 96%, at least about 97%, at least about 98%, at least about 99%, or 100% identical to SEQ ID NO:1. In each of these embodiments, the nucleic acid molecule can be a modified nucleic acid molecule. In some embodiments, the nucleic acid molecule consists of up to about 90 nucleobases and comprises a nucleotide sequence that is at least about 90% identical to SEQ ID NO: 1. In some embodiments, the nucleic acid molecule comprises SEQ ID NO: 1. In some embodiments, the nucleic acid molecule consists of SEQ ID NO: 1.

In some embodiments, the nucleic acid molecule consists of up to about 35 nucleobases and comprises a nucleotide sequence that is at least about 80% identical to SEQ ID NO:2. In some embodiments, the nucleic acid molecule consists of up to about 30 nucleobases, or up to about 25 nucleobases. In some embodiments, the nucleic acid molecule consists of 24 to 35 linked nucleobases, of 24 to 30 linked nucleobases, or 24 to 27 linked nucleobases. In some embodiments, the nucleic acid molecule comprises a nucleotide sequence that is at least about 80%, at least about 85%, at least about 90%, at least about 95%, at least about 96%, at least about 97%, at least about 98%, at least about 99%, or 100% identical to SEQ ID NO:2. In each of these embodiments, the nucleic acid molecule can be a modified nucleic acid molecule. In some embodiments, the nucleic acid molecule consists of up to about 35 nucleobases and comprises a nucleotide sequence that is at least about 90% identical to SEQ ID NO:2. In some embodiments, the nucleic acid molecule comprises SEQ ID NO:2. In some embodiments, the nucleic acid molecule consists of SEQ ID NO:2.

In some embodiments, the nucleobase sequence of the nucleic acid molecule has no more than two mismatches compared to a nucleobase sequence of SEQ ID NO:1 or SEQ ID NO:2. In some embodiments, the nucleobase sequence of the nucleic acid molecule has no more than one mismatch compared to a nucleobase sequence of SEQ ID NO:1 or SEQ ID NO:2. In some embodiments, the nucleobase sequence of the nucleic acid molecule has one mismatch compared to a nucleobase sequence of SEQ ID NO:1 or SEQ ID NO:2. In some embodiments, the nucleobase sequence of the nucleic acid molecule has no mismatches compared to a nucleobase sequence of SEQ ID NO:1 or SEQ ID NO:2. In each of these embodiments, the nucleic acid molecule can be a modified nucleic acid molecule.

Suitable nucleic acids include, but are not limited to, deoxyribonucleic acid (DNA), ribonucleic acid (RNA), modified DNA or RNA, peptide nucleic acid (PNA), morpholino, locked nucleic acid (LNA), glycol nucleic acid (GNA), threose nucleic acid (TNA), DNA containing phosphorothioate residues (S-oligos) and derivatives thereof, or any combination thereof.

In some embodiments, one or more additional nucleobases may be added to either or both of the 3' terminus and 5' terminus of a nucleic acid molecule in comparison to the nucleobases sequences of SEQ ID NO:1 or SEQ ID NO:2. In some embodiments, the one or more additional linked nucleobases are at the 3' terminus. In some embodiments, the one or more additional linked nucleosides are at the 5' terminus. In some embodiments, two additional linked nucleosides are linked to a terminus. In some embodiments, one additional nucleoside is linked to a terminus. In each of these embodiments, the nucleic acid molecule can be a modified nucleic acid molecule.

In some embodiments, the nucleic acid molecule comprises one or more modified internucleoside linkages, modified sugars, or modified nucleobases, or any combination thereof. The nucleobase sequences set forth herein, including but not limited to those found in the Examples and in the sequence listing, are independent of any modification to the nucleic acid molecule. As such, nucleic acid molecules defined by a SEQ ID NO: may comprise, independently, one or more modifications to one or more sugar moieties, to one or more internucleoside linkages, and/or to one or more nucleobases. A modified nucleobase, sugar, and/or internucleoside linkage may be selected over an unmodified form because of desirable properties such as, for example, enhanced cellular uptake, enhanced affinity for other nucleic acid molecules or nucleic acid targets and increased stability in the presence of nucleases.

In some embodiments, at least one internucleoside linkage is a modified internucleoside linkage. In some embodiments, each internucleoside linkage is a modified internucleoside linkage. In some embodiments, a modified internucleoside linkage comprises a phosphorus atom. In some embodiments, a modified nucleic acid molecule comprises at least one phosphorothioate internucleoside linkage. In some embodiments, each internucleoside linkage of a modified nucleic acid molecule is a phosphorothioate internucleoside linkage. In some embodiments, a modified internucleoside linkage does not comprise a phosphorus atom. In some such embodiments, an internucleoside linkage is formed by a short chain alkyl internucleoside linkage. In some such embodiments, an internucleoside linkage is formed by a cycloalkyl internucleoside linkages. In some such embodiments, an internucleoside linkage is formed by a mixed heteroatom and alkyl internucleoside linkage. In some such embodiments, an internucleoside linkage is formed by a mixed heteroatom and cycloalkyl internucleoside linkages. In some such embodiments, an internucleoside linkage is formed by one or more short chain heteroatomic internucleoside linkages. In some such embodiments, an internucleoside linkage is formed by one or more heterocyclic internucleoside linkages. In some such embodiments, an internucleoside linkage has an amide backbone. In some such embodiments, an internucleoside linkage has mixed N, O, S and $CH_2$ component parts.

In some embodiments, at least one nucleobase of the modified nucleic acid molecule comprises a modified sugar. In some embodiments, each of a plurality of nucleosides comprises a modified sugar. In some embodiments, each nucleoside of the modified nucleic acid molecule comprises a modified sugar. In each of these embodiments, the modified sugar may be a 2'-O-methoxyethyl sugar, a 2'-fluoro sugar, a 2-O-methyl sugar, or a bicyclic sugar moiety. In some embodiments, each of a plurality of nucleosides comprises a 2'-O-methoxyethyl sugar and each of a plurality of nucleosides comprises a 2'-fluoro sugar.

In some embodiments, the sugar-modified nucleosides can further comprise a natural or modified heterocyclic base moiety and/or a natural or modified internucleoside linkage and may include further modifications independent from the sugar modification. In some embodiments, a sugar modified nucleoside is a 2'-modified nucleoside, wherein the sugar ring is modified at the 2' carbon from natural ribose or 2'-deoxyribose.

In some embodiments, a 2'-modified nucleoside has a bicyclic sugar moiety. In some such embodiments, the bicyclic sugar moiety is a D sugar in the alpha configuration. In some such embodiments, the bicyclic sugar moiety is a D sugar in the beta configuration. In some such embodiments, the bicyclic sugar moiety is an L sugar in the alpha configuration. In some such embodiments, the bicyclic sugar moiety is an L sugar in the beta configuration. In some embodiments, the bicyclic sugar moiety comprises a bridge group between the 2' and the 4'-carbon atoms. In some such embodiments, the bridge group comprises from 1 to 8 linked biradical groups. In some embodiments, the bicyclic sugar moiety comprises from 1 to 4 linked biradical groups. In some embodiments, the bicyclic sugar moiety comprises 2 or 3 linked biradical groups. In some embodiments, the bicyclic sugar moiety comprises 2 linked biradical groups. Biradical groups are well known in the art.

In some embodiments, the modified nucleic acid molecule comprises at least one modified nucleobase. In some embodiments, the modified nucleobase is selected from 5-hydroxymethyl cytosine, 7-deazaguanine and 7-deazaadenine. In some embodiments, the modified nucleobase is selected from 7-deaza-adenine, 7-deazaguanosine, 2-aminopyridine and 2-pyridone. In some embodiments, the modified nucleobase is selected from 5-substituted pyrimidines, 6-azapyrimidines and N-2, N-6 and 0-6 substituted purines, including 2 aminopropyladenine, 5-propynyluracil and 5-propynylcytosine. In some embodiments, the modified nucleobase is a 5-methylcytosine. In some embodiments, at least one nucleoside comprises a cytosine, wherein the cytosine is a 5-methylcytosine. In some embodiments, each cytosine is a 5-methylcytosine.

In some embodiments, a 2'-modified nucleoside comprises a 2'-substituent group selected from halo, allyl, amino, azido, —SH, —CN, —OCN, —CF$_3$, —OCF$_3$, —O—, —S—, or —N(R$_m$)-alkyl; —O—, —S—, or —N(R$_m$)-alkenyl; —O—, —S— or —N(R$_m$)-alkynyl; —O-alkylenyl-O-alkyl, alkynyl, alkaryl, aralkyl, —O-alkaryl, —O-aralkyl, —O(CH$_2$)$_2$SCH$_3$, —O—(CH$_2$)$_2$—O—N(R$_m$)(R$_n$) or —O—CH$_2$—C(=O)—N(R$_m$)(R$_n$), where each R$_m$ and R$_n$ is, independently, H, an amino protecting group or substituted or unsubstituted C$_{1-10}$alkyl. These 2'-substituent groups can be further substituted with one or more substituent groups independently selected from hydroxyl, amino, alkoxy, carboxy, benzyl, phenyl, nitro, thiol, thioalkoxy, halogen, alkyl, aryl, alkenyl and alkynyl.

In some embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), —O(CH$_2$)$_2$O(CH$_2$)$_2$N(CH$_3$)$_2$, and N-substituted acetamide (O—CH$_2$—C(=O)—N(Rm)(R$_n$) where each R$_m$ and R$_n$ is, independently, H, an amino protecting group or substituted or unsubstituted C$_{1-10}$alkyl. In some embodiments, a 2'-modified nucleoside comprises a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In some embodiments, a 2'-modified nucleoside comprises a 2'-substituent group selected from F, O—CH$_3$, and OCH$_2$CH$_2$OCH$_3$. In some embodiments, a sugar-modified nucleoside is a 4'-thio modified nucleoside. In some embodiments, a sugar-modified nucleoside is a 4'-thio-2'-modified nucleoside. A 4'-thio modified nucleoside has a B-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-OCH$_3$, 2'-O—(CH$_2$)$_2$—OCH$_3$, and 2'-F.

In some embodiments, a modified nucleobase comprises a polycyclic heterocycle. In some embodiments, a modified nucleobase comprises a tricyclic heterocycle. In some embodiments, a modified nucleobase comprises a phenoxazine derivative. In some embodiments, the phenoxazine can be further modified to form a nucleobase known in the art as a G-clamp.

In some embodiments, the nucleic acid molecule comprises a modified nucleic acid molecule conjugated to one or more moieties which enhance the activity, cellular distribution or cellular uptake of the resulting nucleic acid molecule. In some such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In some embodiments, a conjugate group is attached directly to a modified nucleic acid molecule. In some embodiments, a conjugate group is attached to a modified nucleic acid molecule by a linking moiety selected from amino, hydroxyl, carboxylic acid, thiol, unsaturations (e.g., double or triple bonds), 8-amino-3,6-dioxaoctanoic acid (ADO), succinimidyl4-(N-maleimidomethyl)cyclohexane-1-carboxylate (SMCC), 6-aminohexanoic acid (AHEX or AHA), substituted C$_{1-10}$alkyl, substituted or unsubstituted C$_{2-10}$alkenyl, and substituted or unsubstituted C$_{2-10}$alkynyl. In some such embodiments, a substituent group is selected from hydroxyl, amino, alkoxy, carboxy, benzyl, phenyl, nitro, thiol, thioalkoxy, halogen, alkyl, aryl, alkenyl and alkynyl.

In some such embodiments, the nucleic acid molecule comprises a modified nucleic acid molecule having one or more stabilizing groups that are attached to one or both termini of a modified nucleic acid molecule to enhance properties such as, for example, nuclease stability. Included in stabilizing groups are cap structures. These terminal modifications protect a modified nucleic acid molecule from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps. Additional cap structures include, but are not limited to, a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentafuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

The at least one pharmaceutical agent present in the composition with the above-described nucleic acid molecule(s) can be any pharmaceutical agent that upregulates TNF-related apoptosis-inducing ligand (TRAIL) or activates the TRAIL signaling pathway. In some embodiments, the pharmaceutical agent is rhTRAIL, PEG-TRAIL, His-TRAIL, Flag-TRAIL, TRA-8, AMG-655, TIC1, TIC2, TIC4, TIC5, TIC6, TIC7, TIC78 TIC9, TIC10 (ONC201), apomab, mapatumumab, and/or lexatumumab, or any combination thereof. In some embodiments, the pharmaceutical agent is rhTRAIL, TIC10 (ONC201), apomab, mapatumumab, and/or lexatumumab, or any combination thereof. In some embodiments, the pharmaceutical agent is rhTRAIL, TIC10 (ONC201), mapatumumab, and/or lexatumumab, or any combination thereof. In some embodiments, the pharmaceutical agent is rhTRAIL. In some embodiments, the pharmaceutical agent is TIC10 (ONC201). In some embodiments, the pharmaceutical agent is mapatumumab. In some embodiments, the pharmaceutical agent is lexatumumab. In some embodiments, the pharmaceutical agent is stem-cell based TRAIL delivery, TRAIL-loaded nanoliposomes or leukocytes, and/or TRAIL nanoparticle delivery.

In some embodiments, the pharmaceutical composition comprises a pharmaceutically acceptable carrier or diluent. In some embodiments, the compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid molecule(s) of the composition.

In some embodiments, pharmaceutical compositions comprise one or more modified nucleic acid molecules and one or more excipients. In some such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In some embodiments, the pharmaceutical compositions comprise an adjuvant. In some embodiments, the adjuvant is selected from mineral oil, vegetable oils, alum, 1018 ISS, aluminum salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, an interleukin (such as, IL-2, IL-13, IL-21), Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) (PLG)-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, and Superfos. In some embodiments, the adjuvant is Freund's or GM-CSF.

In some embodiments, a pharmaceutical composition is prepared using known techniques, including, but not limited to mixing, dissolving, granulating, dragee-making, levigating, emulsifying, encapsulating, entrapping or tab letting processes.

In some embodiments, a pharmaceutical composition is a liquid (e.g., a suspension, elixir and/or solution). In some such embodiments, a liquid pharmaceutical composition is prepared using ingredients known in the art, including, but not limited to, water, glycols, oils, alcohols, flavoring agents, preservatives, and coloring agents.

In some embodiments, a pharmaceutical composition is a solid (e.g., a powder, tablet, and/or capsule). In some such embodiments, a solid pharmaceutical composition comprising one or more nucleic acid molecules is prepared using ingredients known in the art, including, but not limited to, starches, sugars, diluents, granulating agents, lubricants, binders, and disintegrating agents.

In some embodiments, a pharmaceutical composition is formulated as a depot preparation. Some such depot preparations are typically longer acting than non-depot preparations. In some embodiments, such preparations are administered by implantation (for example subcutaneously or intramuscularly) or by intramuscular injection. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

In some embodiments, a pharmaceutical composition comprises a delivery system. Examples of delivery systems include, but are not limited to, liposomes and emulsions. Delivery systems are useful for preparing pharmaceutical compositions including those comprising hydrophobic compounds. In some embodiments, some organic solvents such as dimethylsulfoxide are used. In some embodiments, presently available RNAi packaging technology can be used to packing the miRNA in lipid complexes and to deliver the miRNA. The delivery system can also comprise nanoparticles or nano-complexes. The delivery system can also comprise bacterial mini-cells comprising RNA duplexes.

In some embodiments, a pharmaceutical composition comprises one or more tissue-specific delivery molecules designed to deliver the one or more nucleic acid molecule(s) and pharmaceutical agents to specific tissues or cell types. For example, in some embodiments, pharmaceutical compositions include liposomes coated with a tissue-specific antibody.

In some embodiments, a pharmaceutical composition comprises a cosolvent system. Some such co-solvent systems comprise, for example, benzyl alcohol, a nonpolar surfactant, a water-miscible organic polymer, and an aqueous phase. In some embodiments, such cosolvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some embodiments, a pharmaceutical composition comprises a sustained-release system. A non-limiting example of such a sustained-release system is a semipermeable matrix of solid hydrophobic polymers. In some embodiments, sustained-release systems may, depending on their chemical nature, release pharmaceutical agents over a period of hours, days, weeks or months.

In some embodiments, a pharmaceutical composition is prepared for oral administration. In some such embodiments, a pharmaceutical composition is formulated by combining one or more compounds comprising any one or more of the nucleic acid molecules described herein with one or more pharmaceutically acceptable carriers. Some such carriers enable pharmaceutical compositions to be formulated as tablets, pills, dragees, capsules, liquids, gels, syrups, slurries, suspensions and the like, for oral ingestion by a subject. In some embodiments, pharmaceutical compositions for oral use are obtained by mixing the nucleic acid molecule and one or more solid excipients. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, such a mixture is optionally ground and auxiliaries are optionally added. In some embodiments, pharmaceutical compositions are formed to obtain tablets or dragee cores. In some embodiments, disintegrating agents (e.g., cross-linked polyvinylpyrrolidone, agar, or alginic acid or a salt thereof, such as sodium alginate) are added.

In some embodiments, dragee cores are provided with coatings. In some such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In some embodiments, pharmaceutical compositions for oral administration are push-fit capsules made of gelatin. Some such push-fit capsules comprise one or more of the nucleic acid molecules described herein in admixture with one or more filler such as lactose, binders such as starches, and/or lubricants such as talc or magnesium stearate and, optionally, stabilizers. In some embodiments, pharmaceutical compositions for oral administration are soft, sealed capsules made of gelatin and a plasticizer, such as glycerol or sorbitol. In some soft capsules, one or more of the nucleic acid molecules described herein are be dissolved or suspended in suitable liquids, such as fatty oils, liquid paraffin, or liquid polyethylene glycols. In addition, stabilizers may be added.

In some embodiments, pharmaceutical compositions are prepared for buccal administration. Some such pharmaceutical compositions are tablets or lozenges formulated in conventional manner.

In some embodiments, a pharmaceutical composition is prepared for administration by injection (e.g., intravenous, intraperitoneal, subcutaneous, intramuscular, etc.). In some such embodiments, a pharmaceutical composition comprises a carrier and is formulated in aqueous solution, such as water or physiologically compatible buffers such as Hanks's solution, Ringer's solution, or physiological saline buffer. In some embodiments, other ingredients are included (e.g., ingredients that aid in solubility or serve as preservatives). In some embodiments, injectable suspensions are prepared using appropriate liquid carriers, suspending agents and the like. Some pharmaceutical compositions for injection are presented in unit dosage form, e.g., in ampoules or in multi-dose containers. Some pharmaceutical compositions for injection are suspensions, solutions or emulsions in oily or aqueous vehicles, and may contain formulatory agents such as suspending, stabilizing and/or dispersing agents. Some solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the oligonucleotides described herein to allow for the preparation of highly concentrated solutions. In some embodiments, a pharmaceutical composition is prepared for transmucosal administration. In some such embodiments penetrants appropriate to the barrier to be permeated are used in the formulation. Such penetrants are generally known in the art.

In some embodiments, a pharmaceutical composition is prepared for administration by inhalation. Some such pharmaceutical compositions for inhalation are prepared in the form of an aerosol spray in a pressurized pack or a nebulizer. Some such pharmaceutical compositions comprise a propellant, e.g., dichlorodifluoromethane, trichlorofluoromethane, dichlorotetrafluoroethane, carbon dioxide or other suitable gas. In some embodiments using a pressurized aerosol, the dosage unit may be determined with a valve that delivers a metered amount. In some embodiments, capsules and cartridges for use in an inhaler or insufflator may be formulated. Some such formulations comprise a powder mixture of one or more of the oligonucleotides described herein and a suitable powder base such as lactose or starch.

In some embodiments, a pharmaceutical composition is prepared for rectal administration, such as a suppositories or retention enema. Some such pharmaceutical compositions comprise known ingredients, such as cocoa butter and/or other glycerides.

In some embodiments, a pharmaceutical composition is prepared for topical administration. Some such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In some embodiments, a pharmaceutical composition comprises a modified nucleic acid molecule in a therapeutically effective amount. In some embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In some embodiments, the pharmaceutical composition may further comprise at least one additional therapeutic agent. The additional therapeutic agent may be another chemotherapeutic agent. In some embodiments, the chemotherapeutic agent is a platinum-based chemotherapeutic agent such as, for example, cisplatin, carboplatin, oxaliplatin, nedaplatin, triplatin tetranitrate, phenanthriplatin, picoplatin, or satraplatin, or any combination thereof. In some embodiments, the another chemotherapeutic agent is tunicamycin, oligomycin, bortezomib, MG132, HDAC inhibitor (MS-275, SAHA), HDAC inhibitor LGP1, 5-flurouracil, cisplatin, sorafenib, or flavopiridol, or any combination thereof. The pharmaceutical compositions may comprise one or more of the additional therapeutic agents.

In some embodiments, the additional therapeutic agent may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and *echinacea*.

The present disclosure also provides methods for treating a cancer comprising administering to a subject in need thereof a nucleic acid molecule consisting of up to about 90 nucleobases and comprising a nucleotide sequence that is at least about 80% identical to SEQ ID NO: 1. In some embodiments, the nucleic acid molecule consists of up to about 85 nucleobases, up to about 80 nucleobases, or up to 75 nucleobases. In some embodiments, the nucleic acid molecule consists of 75 to 90 linked nucleobases, of 75 to 85 linked nucleobases, or 75 to 80 linked nucleobases. In some embodiments, the nucleic acid molecule comprises a nucleotide sequence that is at least about 80%, at least about 85%, at least about 90%, at least about 95%, at least about 96%, at least about 97%, at least about 98%, at least about 99%, or 100% identical to SEQ ID NO:1. In each of these embodiments, the nucleic acid molecule can be a modified nucleic acid molecule. In some embodiments, the nucleic acid molecule consists of up to about 90 nucleobases and comprises a nucleotide sequence that is at least about 90% identical to SEQ ID NO:1. In some embodiments, the nucleic acid molecule comprises SEQ ID NO:1. In some embodiments, the nucleic acid molecule consists of SEQ ID NO: 1. Any of the nucleic acid molecules described herein comprising SEQ ID NO:1 can be administered.

The present disclosure also provides methods for treating a cancer comprising administering to a subject in need thereof a nucleic acid molecule consisting of up to about 35 nucleobases and comprising a nucleotide sequence that is at least about 80% identical to SEQ ID NO:2. In some embodiments, the nucleic acid molecule consists of up to about 30 nucleobases, or up to about 25 nucleobases. In some embodiments, the nucleic acid molecule consists of 24 to 35 linked nucleobases, of 24 to 30 linked nucleobases, or 24 to 27 linked nucleobases. In some embodiments, the nucleic acid molecule comprises a nucleotide sequence that is at least about 80%, at least about 85%, at least about 90%, at least about 95%, at least about 96%, at least about 97%, at least about 98%, at least about 99%, or 100% identical to SEQ ID NO:2. In each of these embodiments, the nucleic acid molecule can be a modified nucleic acid molecule. In some embodiments, the nucleic acid molecule consists of up to about 35 nucleobases and comprises a nucleotide sequence that is at least about 90% identical to SEQ ID NO:2. In some embodiments, the nucleic acid molecule comprises SEQ ID NO:2. In some embodiments, the nucleic acid molecule consists of SEQ ID NO:2. Any of the nucleic acid molecules described herein comprising SEQ ID NO:2 can be administered.

In some embodiments, wherein the subject is administered a nucleic acid molecule comprising SEQ ID NO:1 and/or SEQ ID NO:2 as described herein, the subject is also administered a pharmaceutical agent that upregulates TRAIL or activates TRAIL signaling pathway. Any of the pharmaceutical agents described herein that upregulate TRAIL or activate the TRAIL signaling pathway can be used. For example, in some embodiments, the pharmaceutical agent is rhTRAIL, PEG-TRAIL, His-TRAIL, Flag-TRAIL, TRA-8, AMG-655, TIC1, TIC2, TIC4, TIC5, TIC6, TIC7, TIC78 TIC9, TIC10 (ONC201), apomab, mapatumumab, or lexatumumab, or any combination thereof. In some embodiments, the subject is also administered another chemotherapeutic agent, such as any of the chemotherapeutic agents described herein. In some embodiments, the another chemotherapeutic agent is tunicamycin, oligomycin, bortezomib, MG132, HDAC inhibitor (MS-275, SAHA), HDAC inhibitor LGP1, 5-flurouracil, cisplatin, sorafenib, or flavopiridol, or any combination thereof. The additional therapeutic agent may be administered at the same time, less frequently, or more frequently than one or more of the nucleic acid molecules and/or pharmaceutical agents described herein.

In some embodiments, the cancer is colorectal cancer, ovarian cancer, breast cancer, lung cancer, or melanoma. In some embodiments, the cancer is colorectal cancer. In some embodiments, the cancer is ovarian cancer. In some embodiments, the cancer is breast cancer. In some embodiments, the cancer is lung cancer. In some embodiments, the cancer is melanoma. In some embodiments, the subject has cancer cells having a mutated p53.

In some embodiments, the methods described herein use one or more nucleic acid molecules or modified nucleic acid molecules. The nucleic acid molecules or modified nucleic acid molecules can be administered with or without being integrated into a vector. The nucleic acid molecules or modified nucleic acid molecules can also be used in the form of double stranded entities, whereby the appropriate strand is produced inside a cell.

In some embodiments, administration comprises intravenous administration, subcutaneous administration, intratumoral administration, or intraperitoneal administration.

In some embodiments, any one or more of the nucleic acid molecules described herein is administered at a dose selected from 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, and 800 mg. The nucleic acid molecules may be administered one per day, once per week, once per two weeks, once per three weeks, or once per four weeks.

In some embodiments, the administration of a compound(s) or composition(s) results in reduction of tumor size and/or tumor number. In some embodiments, the administration of a compound(s) or composition(s) prevents an increase in tumor size and/or tumor number. In some embodiments, the administration of a compound(s) or composition(s) prevents, slows, and/or stops metastatic progression. In some embodiments, the administration of a compound(s) or composition(s) extends the overall survival time of the subject. In some embodiments, the administration of a compound(s) or composition(s) extends the progression-free survival of the subject. In some embodiments, administration of a compound(s) or composition(s) prevents the recurrence of tumors. In some embodiments, administration of a compound(s) or composition(s) prevents recurrence of tumor metastasis.

A subject may be diagnosed with a tumor or cancer following the administration of medical tests well known to those in the medical profession. The diagnosis of a tumor or cancer can be made by imaging tests such as ultrasound, helical computed tomography (CT) scan, triple phase CT scan, or magnetic resonance imaging (MRI). The imaging tests allow the assessment of the tumor size, number, location, metastasis, patency and/or invasion of adjacent tissue by the tumor. This assessment aids the decision as to the mode of therapeutic or palliative intervention that is appropriate. The final diagnosis is typically confirmed by needle biopsy and histopathological examination.

In some embodiments, one or more pharmaceutical compositions and one or more other pharmaceutical agents are administered at the same time. In some embodiments, one or more pharmaceutical compositions and one or more other pharmaceutical agents are administered at different times. In some embodiments, one or more pharmaceutical compositions and one or more other pharmaceutical agents are prepared together in a single formulation. In some embodiments, one or more pharmaceutical compositions and one or more other pharmaceutical agents are prepared separately. In some embodiments, the nucleic acid molecule(s) and the pharmaceutical agent(s) that upregulate TRAIL or activate TRAIL signaling pathway are present in a single pharmaceutical composition.

In some embodiments, a pharmaceutical composition is administered in the form of a dosage unit (e.g., tablet, capsule, bolus, etc.). In some embodiments, such pharmaceutical compositions comprise any one or more of the nucleic acid molecules or modified nucleic acid molecules described herein in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In some such embodiments, a pharmaceutical composition comprises a dose of modified nucleic acid molecule selected from 25 mg, 50 mg, 75 mg, 100 mg, 150 mg, 200 mg, 250 mg, 300 mg, 350 mg, 400 mg, 500 mg, 600 mg, 700 mg, and 800 mg. The dosage of the pharmaceutical agents that upregulate TRAIL or activate the TRAIL signaling pathway, and the dosage of the chemotherapeutic agent, is the same dosage clinically used by those skilled in the art.

In some embodiments, the nucleic acid molecule(s) and/or pharmaceutical agent(s), or the compositions containing the same, is sterile lyophilized and is reconstituted with a suitable diluent, e.g., sterile water for injection or sterile saline for injection. The reconstituted product is administered as a subcutaneous injection or as an intravenous infusion after dilution into saline. The lyophilized drug product consists of any one or more of the nucleic acid molecule(s) or modified nucleic acid molecule(s), and/or pharmaceutical agent(s), or the compositions containing the same, described herein which has been prepared in water for injection, or in saline for injection, adjusted to pH 7.0-9.0 with acid or base during preparation, and then lyophilized. The lyophilized modified nucleic acid molecule may be 25-800 mg of any one or more of the nucleic acid molecule(s) or modified nucleic acid molecule(s) described herein. It is understood that this encompasses 25, 50, 75, 100, 125, 150, 175, 200, 225, 250, 275, 300, 325, 350, 375, 425, 450,475, 500, 525, 550,575, 600, 625, 650, 675, 700, 725, 750, 775, and 800 mg of modified lyophilized nucleic acid molecule(s). The lyophilized drug product may be packaged in a 2 mL Type I, clear glass vial (ammonium sulfate-treated), stoppered with a bromobutyl rubber closure and sealed with an aluminum FLIP-OFF® overseal.

The present disclosure also provides methods of detecting and/or determining the level of miR-3132. The detection and/or level determination can be carried out by conventional means known in the art. The level of miR-3132 can be used as disease progress markers for any of the cancers disclosed herein. The miR-3132 can also be used to predict and/or monitor a therapeutic response.

The present disclosure also provides methods of determining whether a subject having cancer is a candidate for miR-3132 treatment, comprising: measuring the amount of miR-3132 in a cancer cell from the subject; wherein if the amount of miR-3132 in the cancer cell from the subject is lower than a threshold amount of miR-3132, then the subject is a candidate for miR-3132 treatment; and wherein if the amount of miR-3132 in the cancer cell from the subject is equal to or greater than a threshold amount of miR-3132, then the subject is not a candidate for miR-3132 treatment. In some embodiments, the threshold amount of miR-3132 is the amount of miR-3132 present in a normal or non-cancerous cell. In some embodiments, the threshold amount of miR-3132 is the amount of miR-3132 that has been established by the medical community as the lowest recommended level. In some embodiments, the cancer cell has a mutated p53. In some embodiments, the subject is sensitive to a pharmaceutical agent that upregulates TRAIL or activates TRAIL signaling pathway, such as any of the pharmaceutical agents described herein.

The present disclosure also provides any one or more of the nucleic acid molecule(s) and/or pharmaceutical agent(s) that upregulates TRAIL or activates TRAIL signaling pathway, or the compositions containing the same, described herein, for use in treating or preventing cancer or a tumor.

The present disclosure also provides any one or more of the nucleic acid molecule(s) and/or pharmaceutical agent(s) that upregulates TRAIL or activates TRAIL signaling pathway, or the compositions containing the same, described herein, for use in the manufacture of a medicament for treating or preventing cancer or a tumor.

The present disclosure also provides uses of any one or more of the nucleic acid molecule(s) and/or pharmaceutical agent(s) that upregulates TRAIL or activates TRAIL signaling pathway, or the compositions containing the same, described herein, for treating or preventing cancer or a tumor.

The present disclosure also provides uses of any one or more of the nucleic acid molecule(s) and/or pharmaceutical agent(s) that upregulates TRAIL or activates TRAIL signaling pathway, or the compositions containing the same, described herein, in the manufacture of a medicament for treating or preventing cancer or a tumor.

The present disclosure also provides any one or more of the nucleic acid molecule(s) and/or pharmaceutical agent(s) that upregulates TRAIL or activates TRAIL signaling pathway, or the compositions containing the same, described herein, or methods of preparing the same, or methods of using the same, or uses any one or more of the nucleic acid molecule(s) and/or pharmaceutical agent(s) that upregulates TRAIL or activates TRAIL signaling pathway, or the compositions containing the same, described herein, substantially as described with reference to the accompanying examples and/or figures.

In order that the subject matter disclosed herein may be more efficiently understood, examples are provided below. It should be understood that these examples are for illustrative purposes only and are not to be construed as limiting the claimed subject matter in any manner.

Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

In order that the subject matter disclosed herein may be more efficiently understood, examples are provided below. It should be understood that these examples are for illustrative purposes only and are not to be construed as limiting the claimed subject matter in any manner.

Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Materials and Methods

Cell Culture and Reagents

All colorectal, breast, and lung cancer cell lines were obtained from American Type Culture Collection (ATCC) and maintained in the recommended media. Cells were routinely verified as free of mycoplasma contamination. miRNA mimics for hsa-miR-3132 (HMI1058) was purchased from Sigma-Aldrich. TRAIL neutralizing antibody RIK2 was purchased from Santa Cruz Biotechnology (sc-56246) and used at a concentration of 1:200 in all experiments. Cleaved Caspase 8 inhibitor Z-IETD-FMK was purchased from BD Biosciences (Cat. no. 550380) and used at final concentration of 10 µM in all experiments.

Transfection of miRNA Mimics miRNA mimic transfections were performed by reverse transfection using Lipofectamine RNAiMAX (Life technologies, Grand Island, NY). miRNA mimics were transfected at concentrations of either 25 nM or 50 or 100 nM, as indicated in respective assays.

Cell Proliferation Assays

A total of 5,000-10,000 cells were transfected with either scrambled duplex or miRNA to a net concentration of 50 nM and plated in a 96-well plate. Cell viability was measured 72 hours post-transfection using CellTiter-Glo® Luminescent Cell Viability Assay (Promega). The percent-cell viability was calculated by normalizing the luminescence signal to scramble duplex wells. All transfections were performed in triplicates and reported as % Viability±SEM, compared to scramble.

Colony Formation Assays

A total of $0.1 \times 10^6$ cells of each cell line were transfected with either scramble duplex or miR-3132 mimics to net concentration of 50 nM for 72 hours. At 72 hours, transfected cells were harvested and 500 cells per treatment group were plated in triplicate in 6-well plates for colony formation. Colonies were stained with 0.25% crystal violet on Day 14, imaged, counted and reported as # of colonies ±SEM.

Cell Cycle Analysis

All cell lines were transfected with either scrambled duplex or miRNA mimic. At 72 hours post-transfection, both floating and adherent cells were collected and fixed in 70% ethanol, followed by RNase A treatment and PI staining. Cell death (sub-G1) was quantified by propidium iodide (PI) staining and flow cytometry. Flow-Jo analysis was performed to quantify the distribution of cells in G1, S, and G2-M phases of the cell cycle under different transfection conditions.

Cell Surface Staining for TRAIL

Cells transfected with SCR or miR-3132 were harvested using enzyme-free cell dissociation buffer (Life Technologies) at indicated time points. Cells were washed with FACS buffer (PBS with 1% FBS and 0.1% sodium azide) and stained with conjugated antibodies against TRAIL (Biolegend, 308205). Flow cytometry data was collected using LSR II flow cytometer (BD Biosciences). Flow-Jo software was used to exclude doublets and analyze data.

Quantitative RT-PCR (qRT-PCR)

Total RNA, which includes miRNA, was isolated using the Quick-RNA™ MiniPrep kit (Zymo Research, Irvine, CA). 1 µg of total RNA from each sample was subjected to cDNA synthesis using SuperScript® III Reverse Transcriptase kit (Life technologies, Grand Island, NY), for detection of target genes and housekeeping genes. For detection of miRNAs, 0.5 µg of total RNA was reverse transcribed using TaqMan® MicroRNA Reverse Transcription Kit (Life technologies, Grand Island, NY). The relative expression of the reported genes and miRNAs was determined using real-time PCR performed on an Applied Biosystems 7900HT Fast Real-Time PCR system. For copy number analysis, a standard curve of miR-3132 copies ranging from $1.56 \times 10^7$ to $1.56 \times 10^{12}$ was used to quantify the copy number of miR-3132 at baseline for each cell lines. GAPDH and RNU6B were used as the endogenous controls for mRNA and miRNA samples, respectively. Each cDNA sample was amplified using Power SYBR Green (Applied Biosystems, CA) and miRNA components were quantified using TaqMan® Universal Master Mix II, no UNG (Applied Biosystems, CA). TaqMan miRNA assays were purchased from Applied Biosystems and used as per the manufacturer's instructions. ΔΔCt analysis was performed to calculate the fold-change for each gene.

Western Blot

Western blotting was performed as described previously. The following antibodies were used: $BCL_{XL}$ (CST, 2764S), PARP (CST, 9542), p53-DO1 (Santa Cruz Biotechnology, sc-126), p21 (Calbiochem, OP64), α-actin (Sigma, A5441), XIAP (CST, 242S), FOXM1 (CST, D12D5), p-FOXM1 (CST, 14170S), Cyclin B1 (Santa Cruz Biotechnology, sc-245), CC3 (CST Asp175, cat. no. 9661), CC8 (CST Asp391, cat. no. 9496) and CC9 (CST Asp330, cat. no. 7237). Secondary antibodies acquired from Jackson Laboratories were horseradish-peroxidase conjugated.

Microarray Analysis

A total of $0.5 \times 10^6$ HT-29 were transfected in duplicate wells with either SCR RNA or 50 nM of miR-3132 mimics for 48 hours. Cells were harvested and RNA was isolated using Quick-RNA™ MiniPrep kit (Zymo Research, Irvine, CA) according to the manufacturer's instructions and submitted to the Fox Chase Cancer Center Genomics Facility for gene expression analyses by microarray. The quality of RNA specimens was determined by Agilent Bioanalyzer RNA kits and RNA was amplified and labeled using the low RNA input linear amplification kit (Agilent, Santa Clara, CA, USA). Labeled cDNA targets were hybridized onto Affymetrix Human Gene 2.0-ST array. Raw data were quantile-normalized using RMA method (Bolstad et al., Bioinformatics, 2003, 19, 185-93). Ratios of gene expression level in miR-3132 transfected versus SCR were calculated and those with at least log 2-fold difference (up or down) were considered genes of interest.

Bioinformatics Analysis

Gene Ontology (GO) analysis was performed to identify overrepresentation of gene ontologies or families in the log 2-fold gene list data. The most enriched ontologies were presented in a pie chart based on both up- and down-regulated genes. Pathway and network analysis by IPA (Ingenuity Pathway Analysis) was performed to identify key biological processes, canonical pathways, upstream transcriptional regulators and gene networks. GSEA (Gene Set Enrichment Analysis) was performed by ranking genes first by highest to lowest log 2-fold change. The ranked gene list was then queried using GSEA software to known Molecular Signature Database (MsigDB). Known pathways from curated databases and published studies that matched our gene signature was then reported in the analysis.

Statistical Analysis

Data are presented as the mean±standard error of the mean from at least three replicates. The Student's two-tailed t-test in GraphPad Prism was used for pairwise analysis. Statistically significant changes (*$p \leq 0.05$, $p \leq 0.01$ and *$\leq 0.001$) are indicated.

Example 2: miR-3132 is Differentially Expressed in Normal, Non-transformed Cells and Cancer Cells miR-3132 is an intronic miRNA transcribed as part of the TMEM198 gene, the function of which remains uncharacterized. In order to understand the role of miR-3132 in cancer, the expression of miR-3132 and its host gene TMEM198 was examined in tumor vs. normal tissue using RNA-seq data from The Cancer Genome Atlas (TCGA). No data was available on miR-3132 for any tumor type. TMEM198 levels were not significantly different in breast tumors as compared to normal tissue (see, FIG. 1, Panel A, first cohort in both graphs). However, contrary to what was predicted, expression of TMEM198 was observed to be higher in CRC and NSCLC tumors when compared to normal tissue (see, FIG. 1, Panel A). Copy number analysis was performed using non-transformed cell lines and cancer cell lines of CRC, breast and lung tissue to measure miR-3132 expression. As seen in FIG. 1, Panel B, miR-3132 expression was observed to be much lower in cancer cells when compared to normal, non-transformed cell lines in all tissue types. HCT-116 cancer line was the only exception that appeared to have higher expression than its normal counterpart.

Referring specifically to FIG. 1: (Panel A) Box indicates the $\log_{10}$ TMEM198 RNA expression from TCGA patient samples in unmatched tumor and normal samples. p-value was obtained from the Kruskal-Wallis test for comparing distributions. (Panel B) Baseline copy number of mature miR-3132 were obtained by converting Ct values in the indicated cell lines to copy number using a standard curve of miR-3132 generated from qRT-PCR of pure material.

Example 3: Expression of miR-3132 has Anti-proliferative and Pro-apoptotic Effects in Cancer Cells The effects of restoring the expression of miR-3132 in cancer cell lines was determined. The short-term and long-term anti-proliferative effects of miR-3132 were examined. Overexpression of miR-3132 showed a broad therapeutic index in all cancer cell lines tested, evident by the 50-80% inhibition in cell viability compared to 5-20% inhibition seen in normal cell lines (see, FIG. 2, Panel A). In a colony formation assay, over 60-90% inhibition of the long-term proliferation of cancer cells was observed (see, FIG. 2, Panels B-D). Thus, miR-3132 has potent anti-proliferative effects. Whether or not miR-3132 could induce cell death in cancer cell lines was also examined. With the exception of MDA-MB-231, at 72 hours post-transfection a 15-45% increase in the subG$_1$ DNA content was observed in all cancer cell lines tested (see, FIG. 3, Panel A). Western blot analysis under similar experimental conditions confirmed these results. Cleavage of PARP and caspase-3 was observed in all cell lines except SW-480 and MD-MBA-231 (see, FIG. 3, Panels B-D). Thus, miR-3132 is a potent anti-proliferative and pro-apoptotic agent with a broad therapeutic index.

Figure 2:
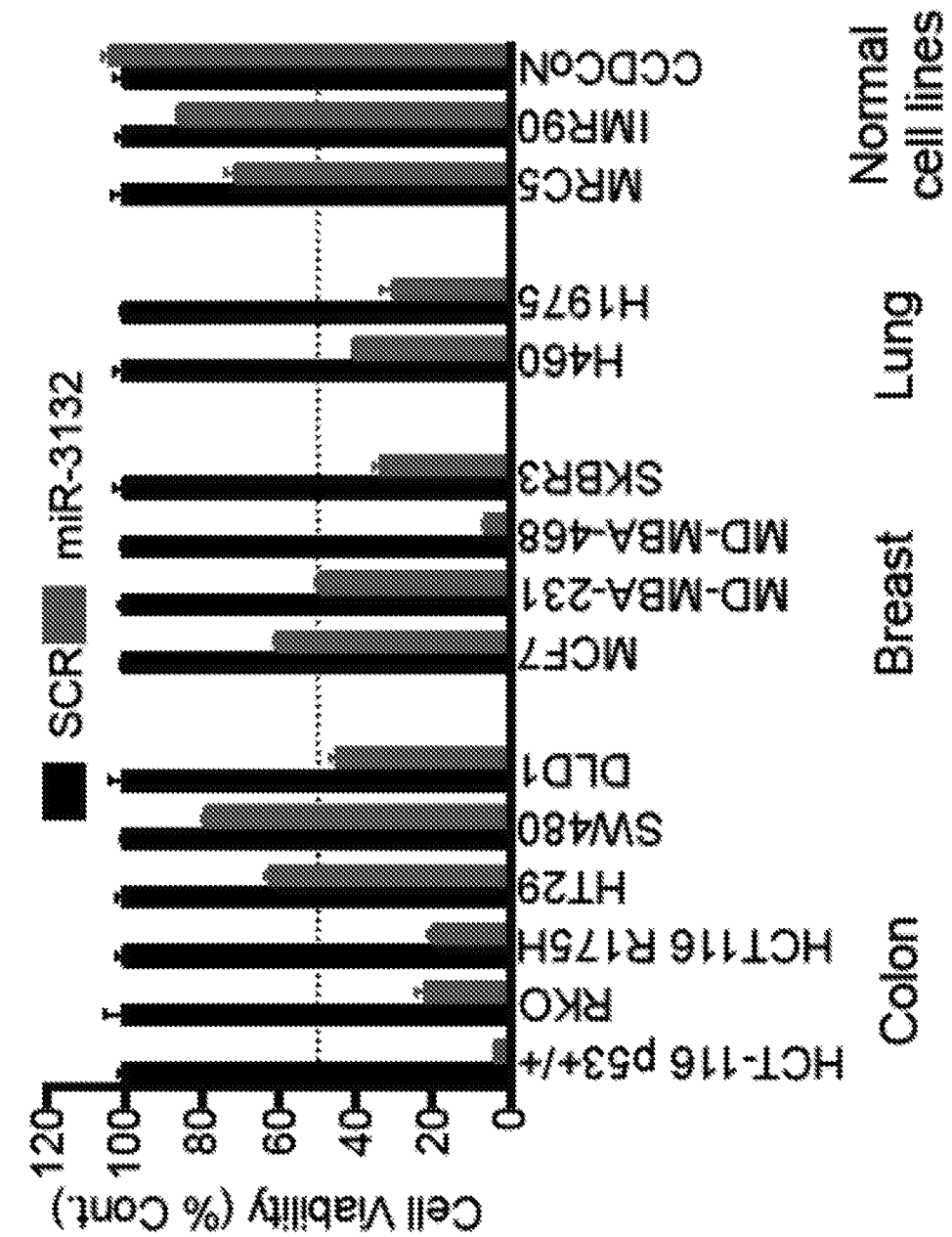
FIG. 2 (Panels A, B, C, and D) shows miR-3132 has potent anti-proliferative effects in cancer cell lines.
Figure 2:
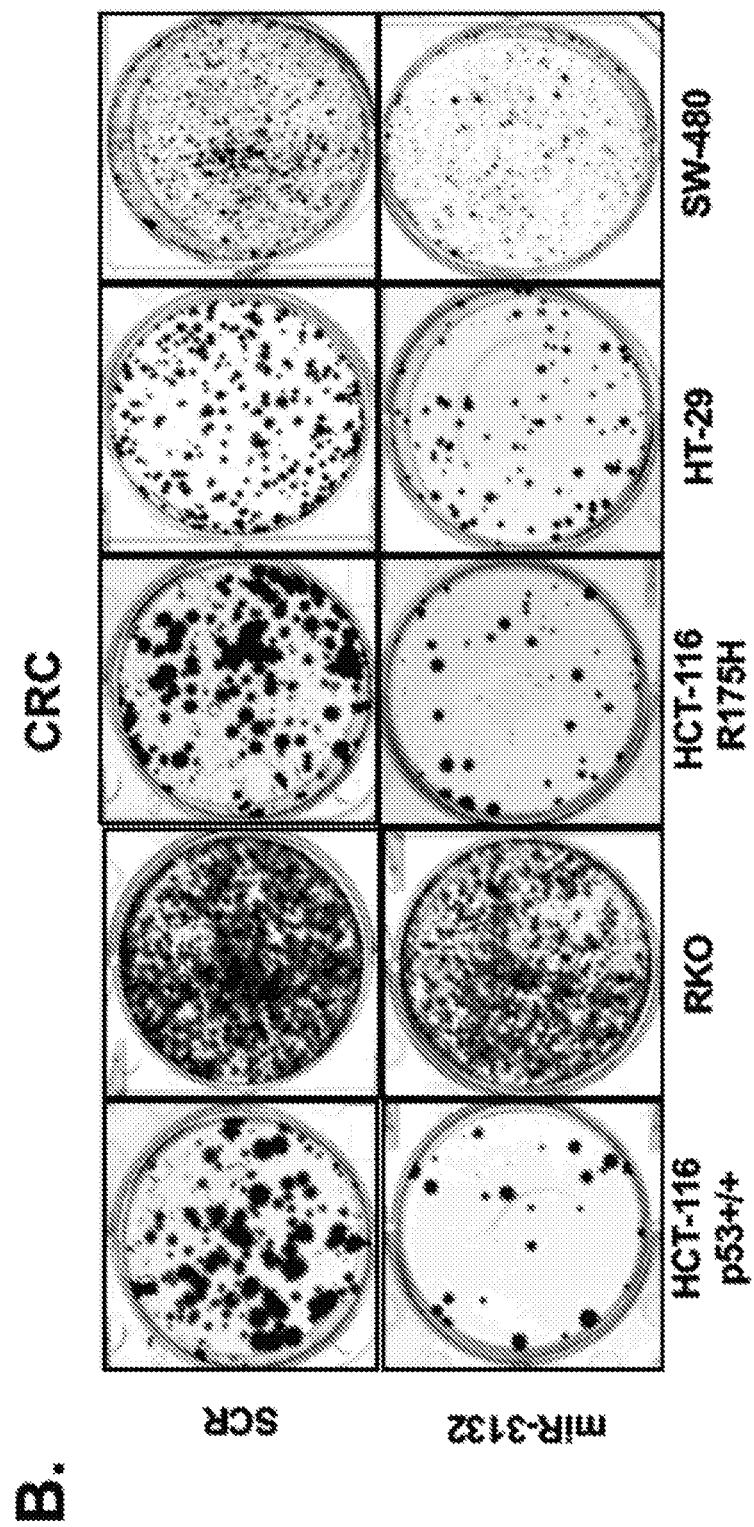
Figure 2:
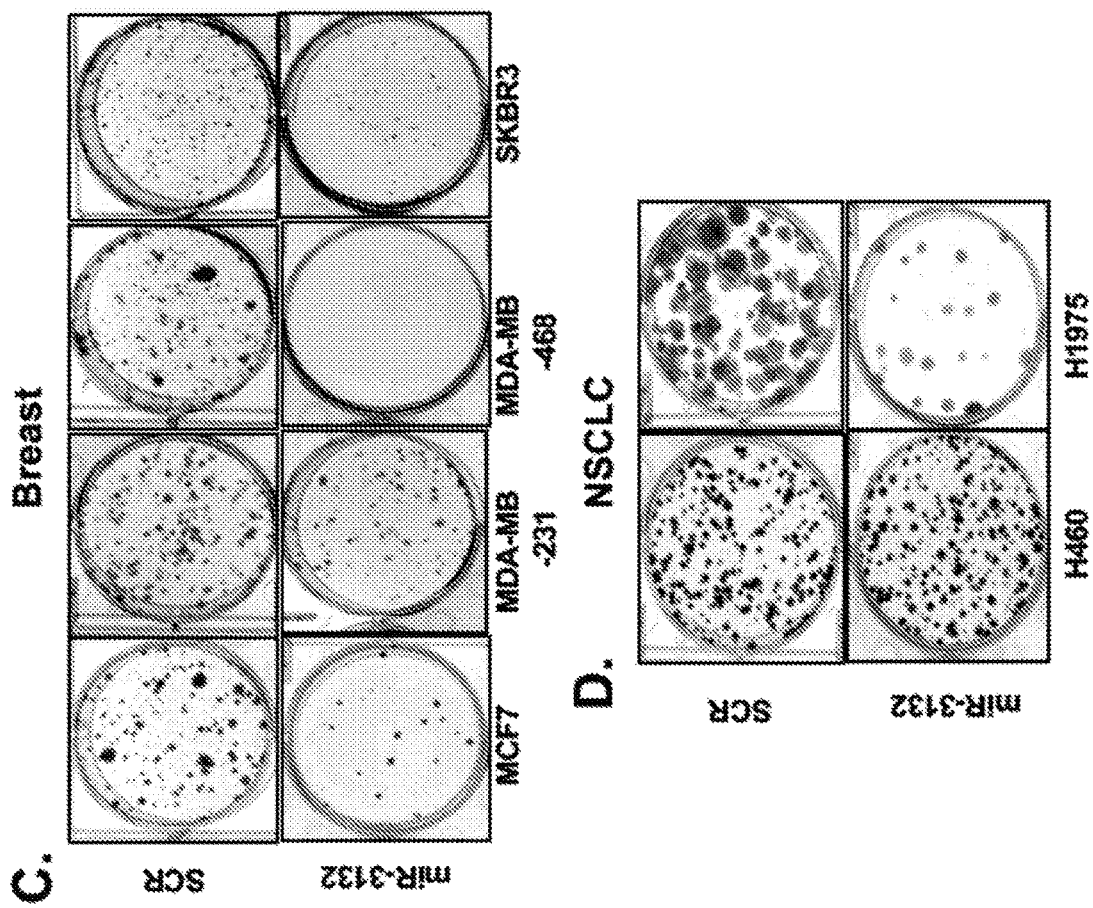

Referring specifically to FIG. 2: (Panel A) A panel of cancer or normal cell lines was transfected with either 50 nM SCR or 50 nM of miR-3132 mimic. Effects on cell viability were measured at 72 hours post-transfection using the CellTiter-Glo assay. (Panels B, C, and D) The effects of the miRNA mimics on long-term cell proliferation of CRC (Panel B), breast (Panel C) and NSCLC (Panel D) cancer cell lines was assessed by colony formation assays done in 6-well plates. Cells were transfected with 50 nM of SCR or miR-3132 mimic. After 72 hours, 500 cells were seeded per well in triplicate for each condition and stained with crystal violet on Day 14. Representative images of cells stained with crystal violet are shown.

Figure 3:
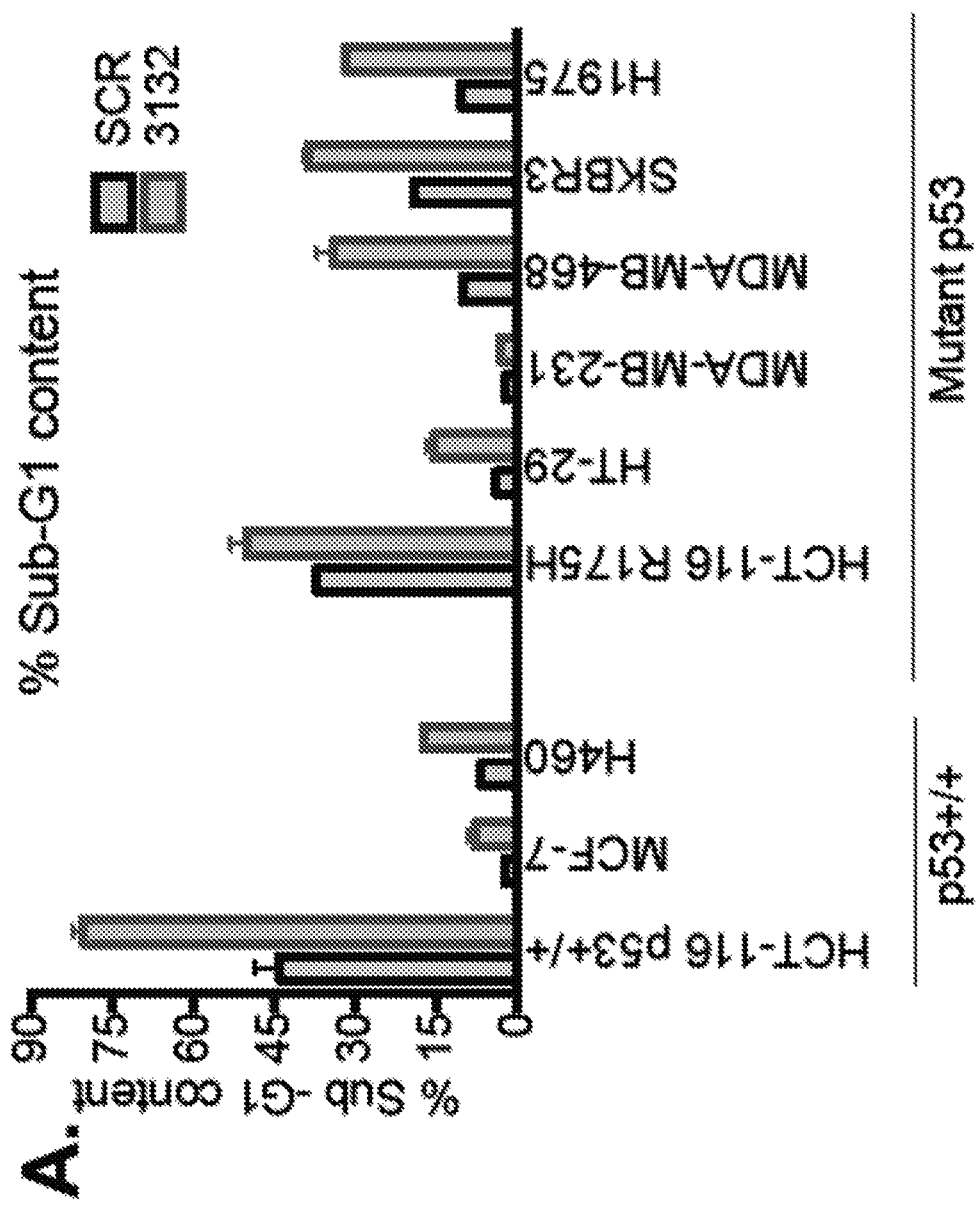
FIG. 3 (Panels A, B, C, and D) shows restoration of miR-3132 induces cell death in cancer cell lines.
Figure 3:
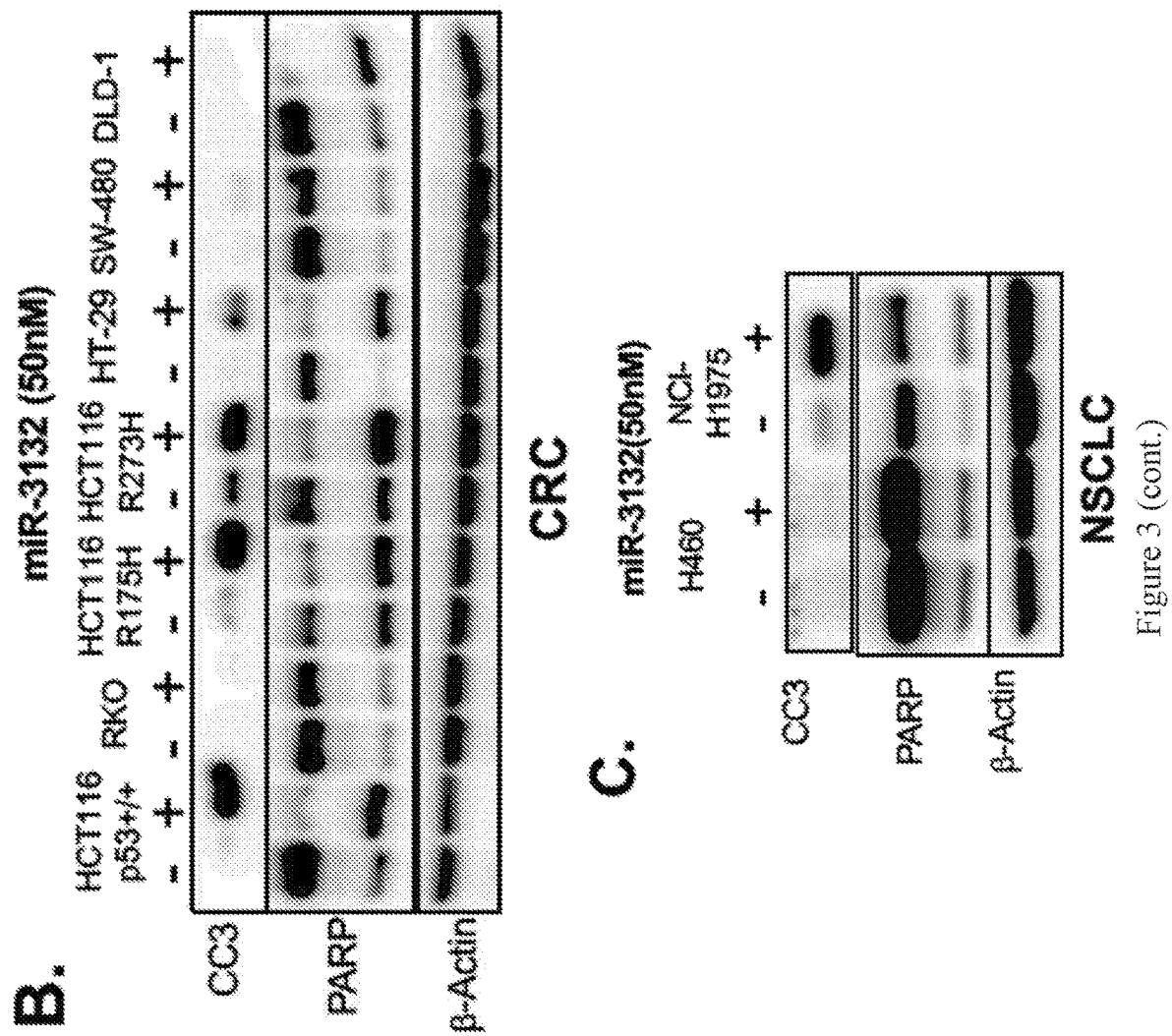
Figure 3:
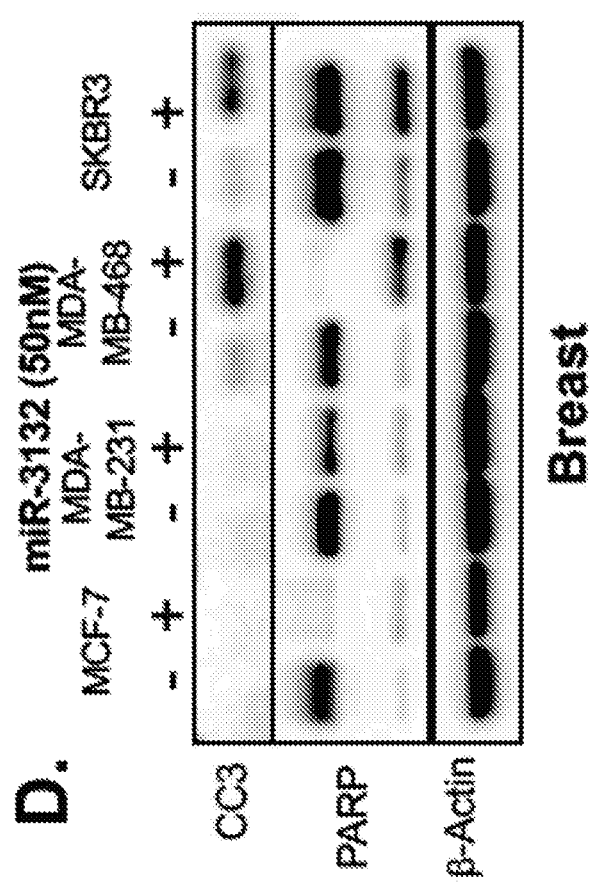

Referring specifically to FIG. 3: (Panel A) Cell cycle profiles and percentage of dead cells (sub-G1) were assessed in the indicated cell lines by transfecting with either SCR or 50 nM miR-3132 mimic. At 72 hours post-transfection cells were fixed, stained with PI and analyzed by FACS. Representative results of changes in sub-G1 phase of cell cycle are graphically represented (n=3). (Panels B, C, and D) Under similar experimental conditions, markers of apoptosis-cleaved levels of PARP and Caspase 3 (CC3) were assessed in CRC (Panel B), NSCLC (Panel C) and breast (Panel D) cancer cell lines.

Figure 4:
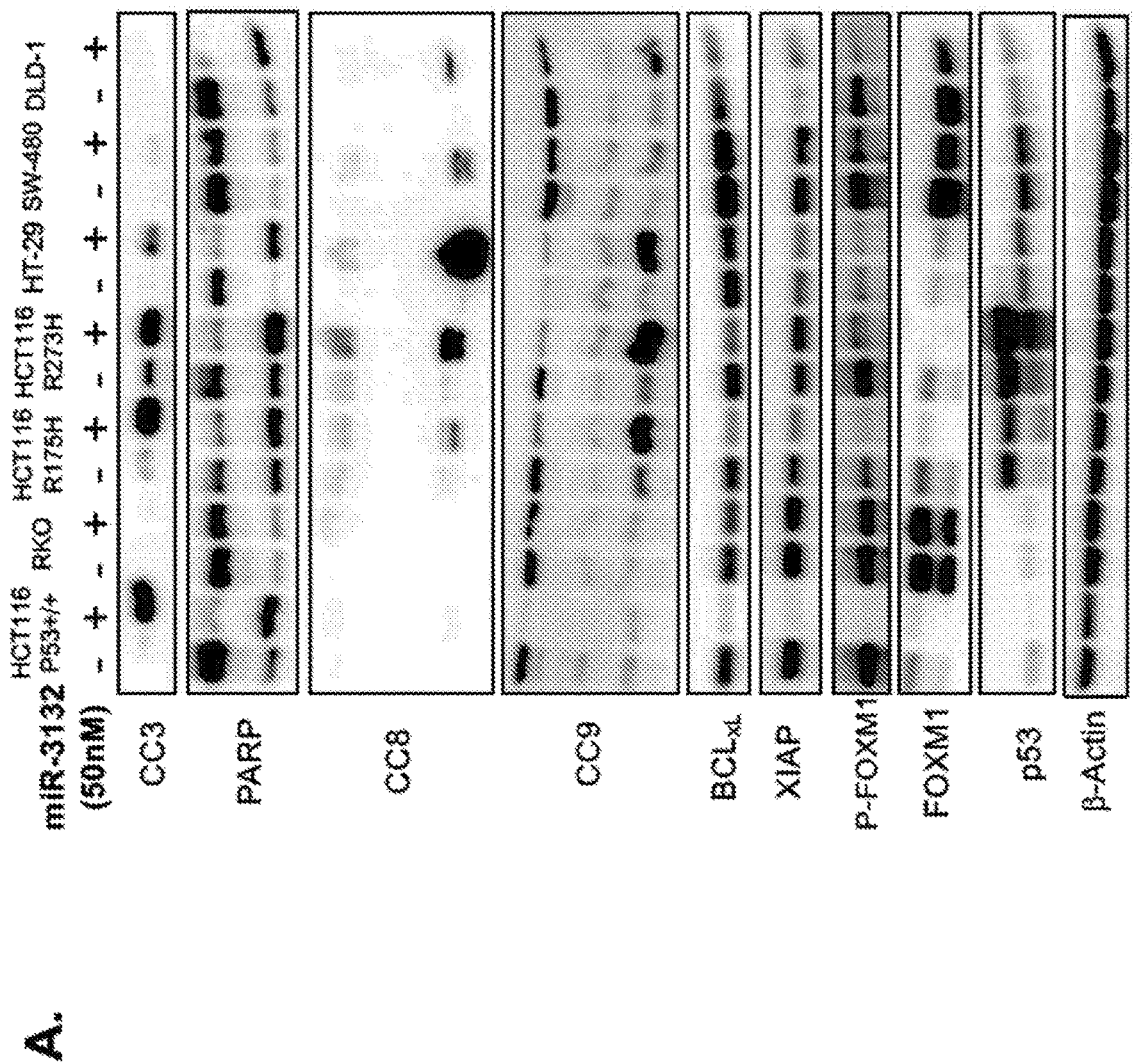
FIG. 4 (Panels A, B, and C) shows miR-3132 engages the extrinsic apoptosis pathway in cancer cell lines.
Figure 4:
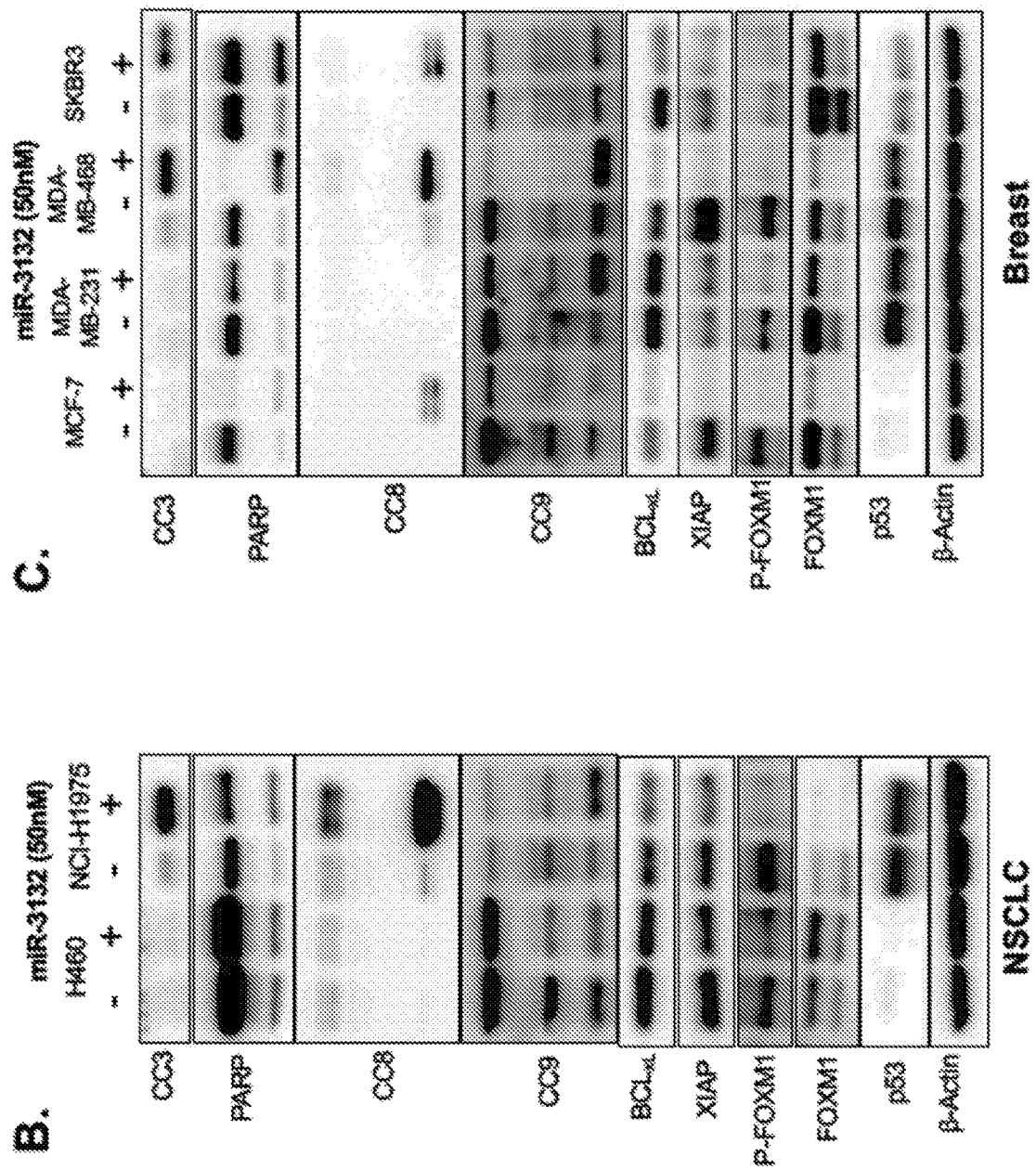

Example 4: miR-3132 Activates the Extrinsic Apoptosis Pathway in Cancer Cell Lines To further characterize the apoptosis induced by miR-3132, a detailed analysis of the different markers of intrinsic and extrinsic apoptosis was carried out. As seen in FIG. 4, Panel A, miR-3132 induced apoptosis through the extrinsic pathway in all CRC cell lines evident by increased levels of cleaved caspase-8. In Type II cell lines such as HCT-116, this further led to increase in cleaved caspase-9 levels and subsequent apoptosis. Of note, apoptosis was p53-independent as seen by unchanged levels of WT p53 in HCT-116 p53$^{+/+}$ cells treated with miR-3132 (see, FIG. 4, Panel A, lanes 1 and 2). Decreases in anti-apoptotic markers, such as BCL$_{xL}$ and XIAP, was also observed. These results were replicated in additional breast cancer cell lines (see, FIG. 4, Panel B) and lung cancer cell lines (see, FIG. 4, Panel C). WT p53 levels were unaltered in both MCF7 (see, FIG. 4, Panel B, lanes 1 and 2) and H460 (see, FIG. 4, Panel C, lanes 1 and 2) cells post miR-3132 treatment, further confirming p53-independent cell death. Overall, 10/13 (excepting RKO, H460 and MD-MBA-231) cell lines were highly sensitive and underwent apoptosis following restoration of miR-3132 expression.

Referring specifically to FIG. 4, cells were transfected with SCR or 50 nM miR-3132 mimic. 72 hours post-transfection cells were harvested and Western blot analysis for different markers of extrinsic and intrinsic were assessed in CRC (Panel A), NSCLC (Panel B) and breast (Panel C) cancer cell lines.

Example 5: miR-3132 Induces TRAIL Expression in Cancer Cells

Having characterized the apoptotic phenotype post miR-3132 treatment, the direct binding targets of miR-3132 was examined in order to gain insight into the pathways that led to sensitivity of the cancer cells to the miRNA. Gene expression profiling was performed using microarray in HT-29 cells to identify a total of 296 genes that were differentially expressed between miR-3132 and control scrambled miR transfected cells (see, FIG. 5, Panel A). Of these 296 genes altered, 98 were down-regulated by log$_2$-fold or lower and 198 genes were up-regulated by log$_2$-fold or higher. This list of 98 genes was compared to predicted miR-3132 targets from TargetScan. Six genes—HOXB9, CDIPT, DESI2, GNAQ, THAP10 and ZXDA—were the predicted targets that overlapped with the down-regulated genes. Experimental validation of these six target genes and additional down-regulated genes with importance in cancer can be carried out, for example, as set forth in FIG. 5, Panel B.

Although the up-regulated list of genes was a primary focus, a surprising 4-fold upregulation of TRAIL (see, FIG. 5, Panel C) was observed, a pro-apoptotic ligand that selectively induces apoptosis in tumor cells. No changes in p53 target genes such as p21, PUMA, NOXA, DR5 was observed in the microarray, confirming that apoptosis was indeed p53 independent.

Figure 5:
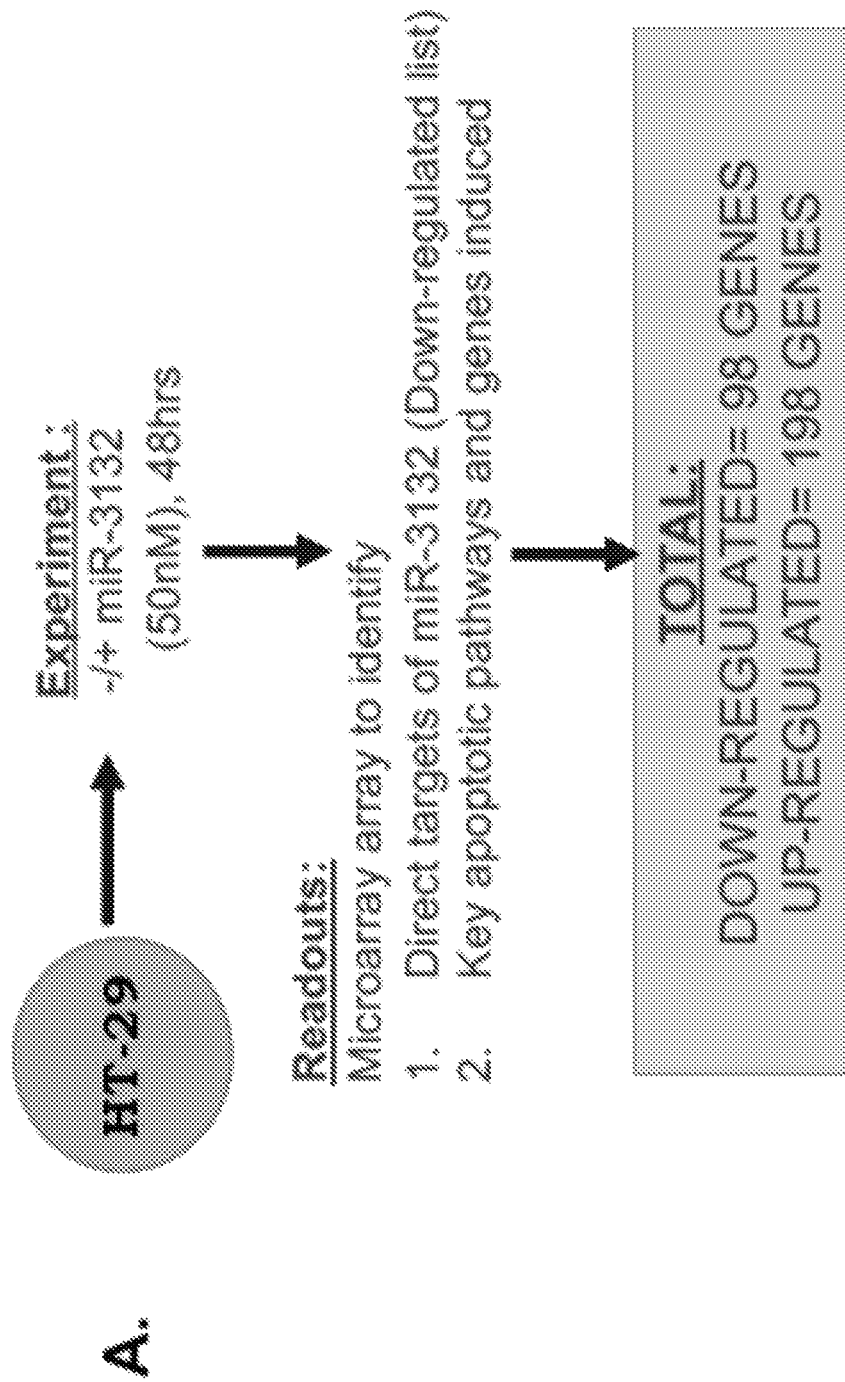
FIG. 5 (Panels A, B, and C) shows miR-3132 induces TRAIL mRNA upregulation by microarray analysis.
Figure 5:
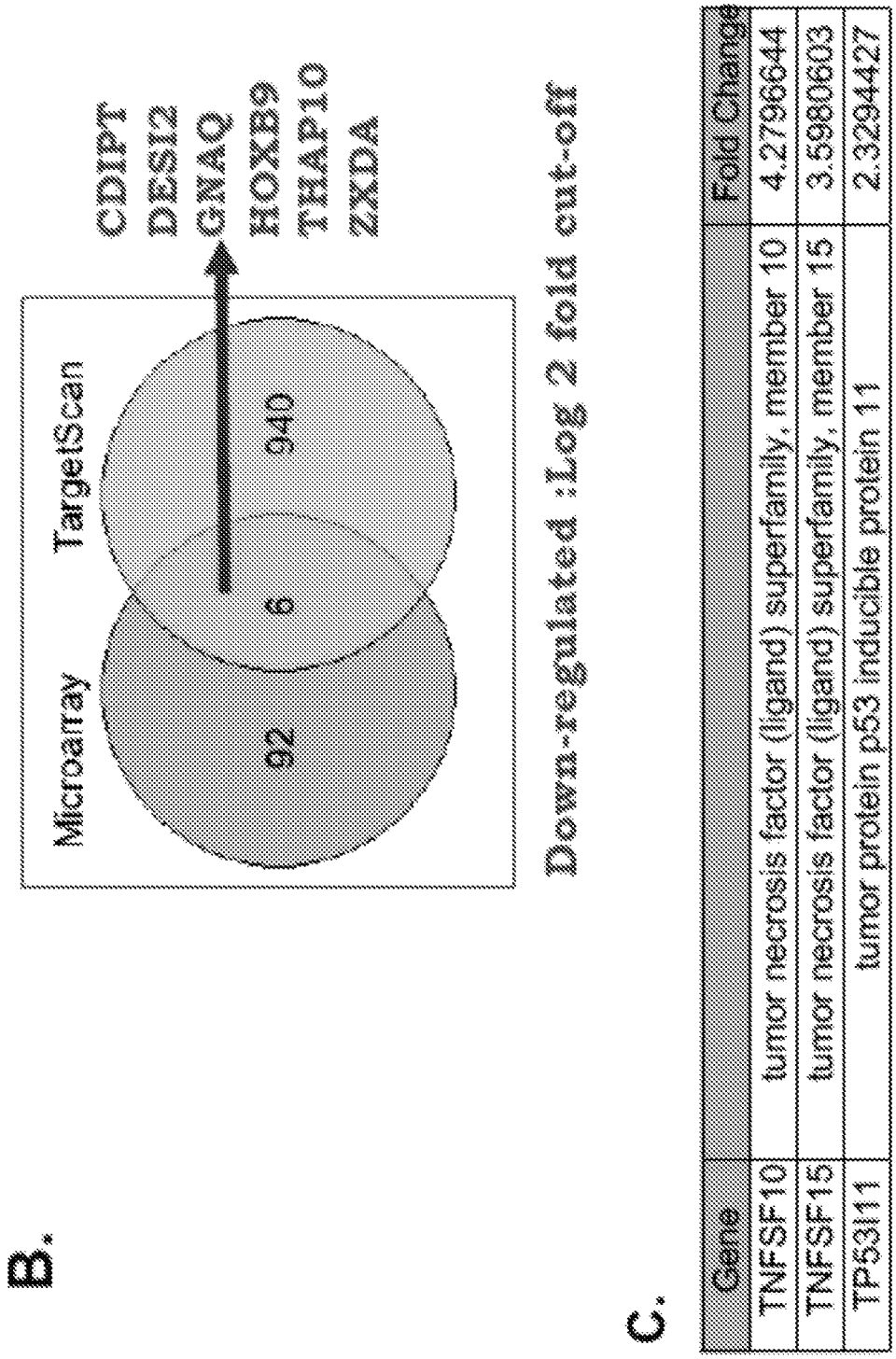

Referring specifically to FIG. 5: (Panel A) Overview of microarray experiment setup, expected readouts and number of genes altered. (Panel B) Venn diagram indicating 6 genes that overlapped between the observed (96) genes down-regulated in microarray and the predicted targets (946) using TargetScan. (Panel C) TRAIL and other key genes linked to apoptosis with their fold change is indicated.

Example 6: Surface TRAIL Upregulation Mediates and is Necessary for miR-3132's Pro-Apoptotic Functions in Cancer Cell Lines To validate the microarray data, whether or not TRAIL was indeed induced at the cell surface in response to miR-3132 was examined. As early as 48 hours post miR-3132 transfection, a robust increase in surface TRAIL was observed in three cell lines examined, HCT-116, HT-29 and SKBR3 (see, FIG. 6, Panels A and B). The surface TRAIL levels were sustained even at 72 hours in the HCT-116 cell line (see, FIG. 6, Panel A). To determine whether or not TRAIL was dispensable for miR-3132 mediated apoptosis through the extrinsic pathway in cancer cells, HCT-116 and HT-29 cell lines were co-treated with miR-3132 mimics and either RIK2 (TRAIL neutralizing antibody) or cleaved caspase-8 inhibitor Z-IETD-FMK. miR-3132 induced cell death, measured by sub-G1 DNA content analysis, was abrogated in presence of RIK2 and Z-IETD-FMK (see, FIG. 6, Panel C). As early as 48 hours post-treatment, both RIK2 and Z-IETD-FMK blocked the miR-3132 induced apoptosis markers cleaved caspase-8 and downstream cleaved caspase-9, cleaved caspase-3, and PARP in HCT-116 cells (see, FIG. 6, Panel D, left). Similar results were observed in HT-29 cells, 72 hours post treatment (see, FIG. 6, Panel D, right). This indicates the TRAIL is required and indispensable for miR-3132 induced apoptosis. It also validates that cell death by miR-3132 is primarily due to engagement of the extrinsic apoptosis pathway.

Figure 6:
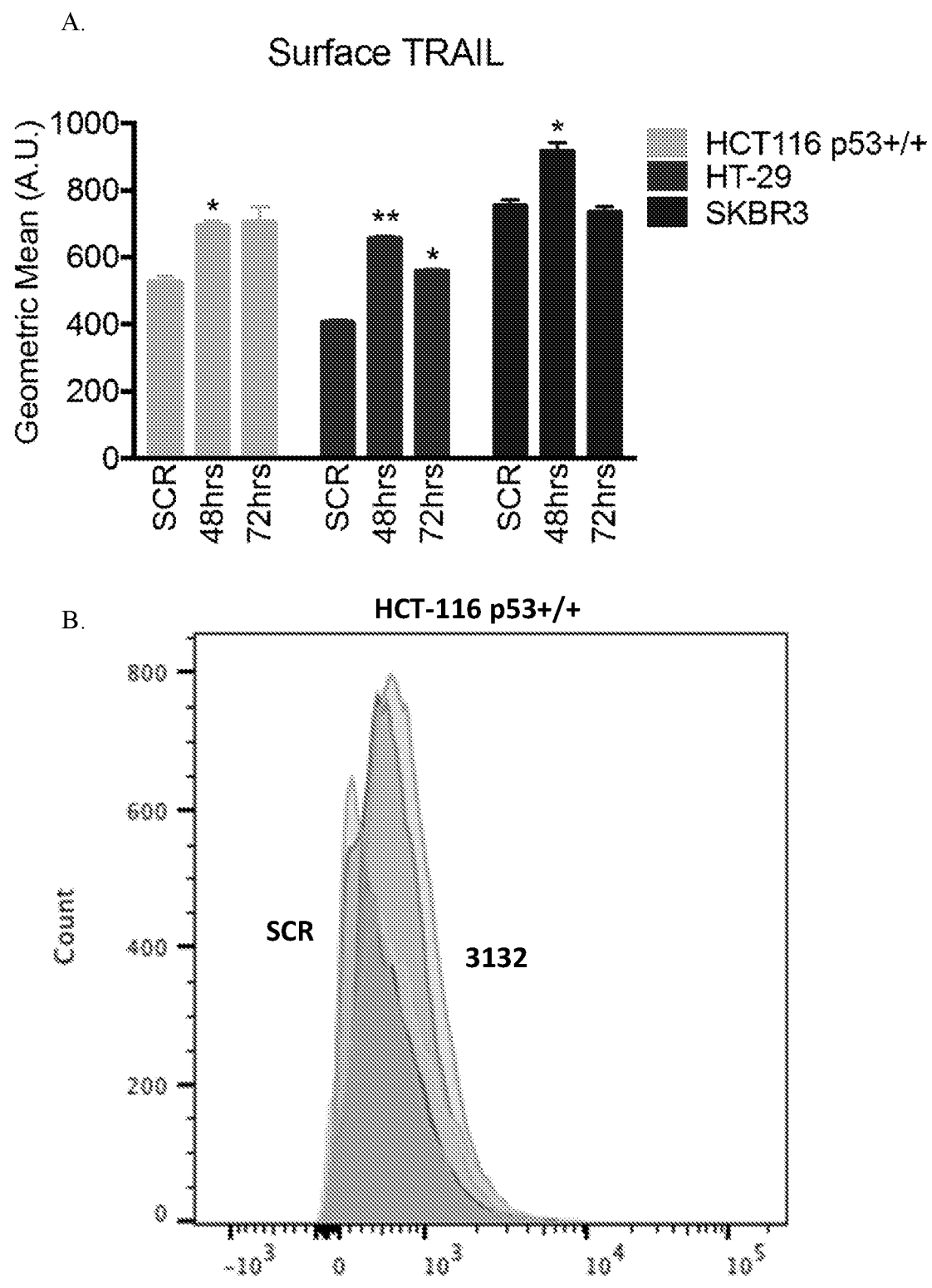
FIG. 6 (Panels A, B, C, and D) shows TRAIL is indispensable for miR-3132 dependent apoptosis.
Figure 6:
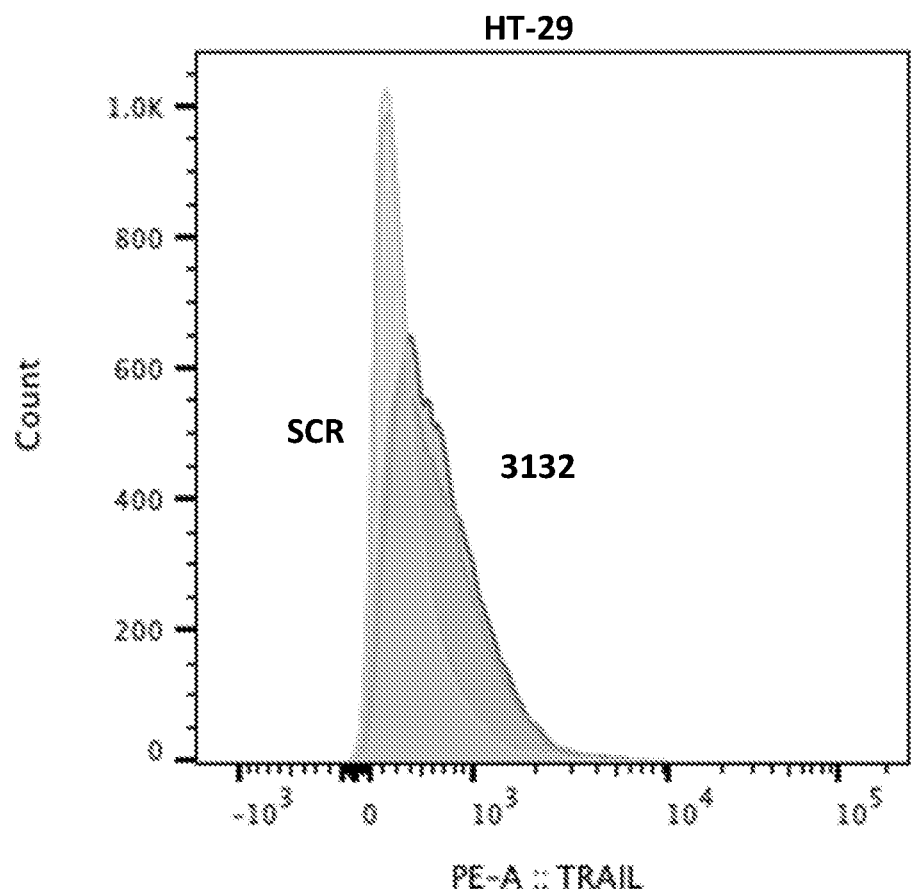
Figure 6:
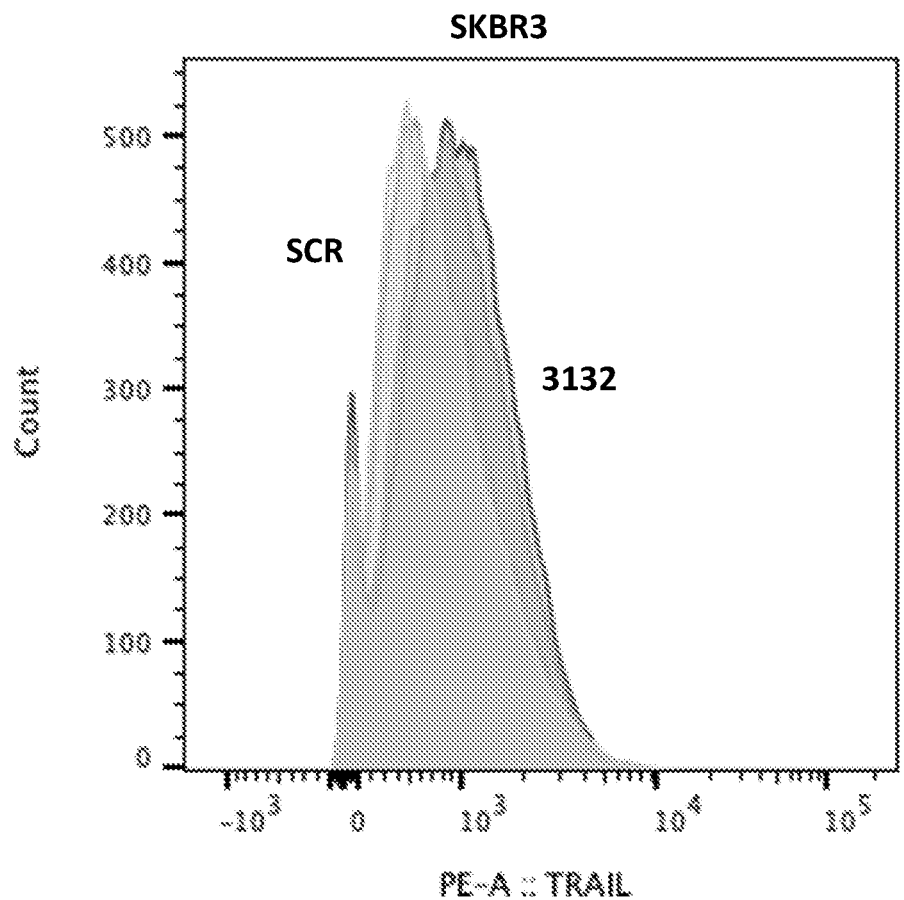
Figure 6:
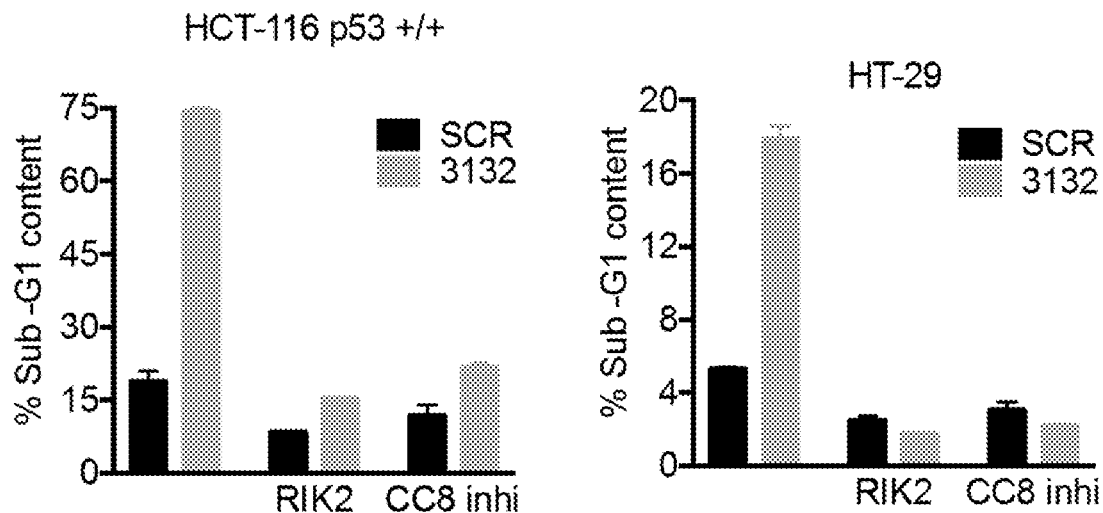
Figure 6:
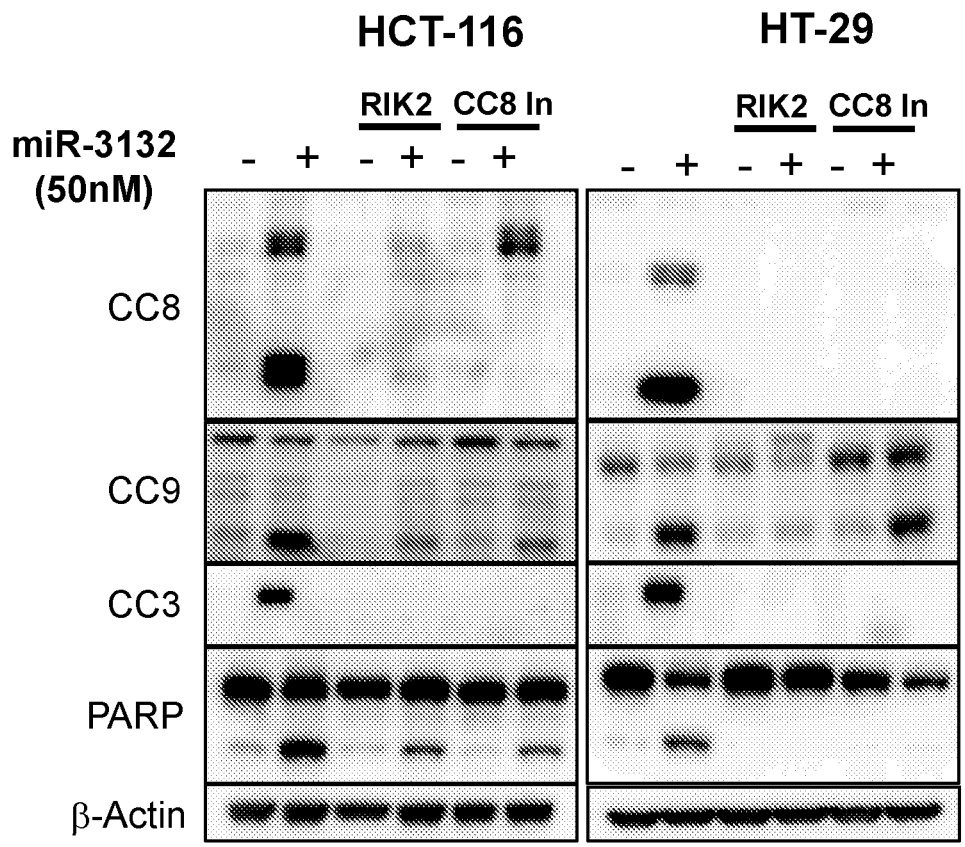

Referring specifically to FIG. 6: (Panel A) Expression of TRAIL at the cell surface post transfection with 50 nM miR-3132 was tested at the indicated times by flow cytometry. Graphs indicate geometric mean (arbitrary units) of TRAIL expression from duplicate samples. (Panel B) Histograms showing the same result as (Panel A), 48 hour time point. Note here, a shift on the X-axis to the right (blue, red) indicates increase in surface TRAIL expression compared to control (light and dark green). Y-axis indicates cell count. (Panel C) Sub-G1 analysis to measure cell death by PI staining was performed 72 hours post co-treatment with miR-3132 and either RIK2 or CC8 inhibitor. (Panel D) Using the same experimental conditions as (Panel C), markers of apoptosis were assessed by Western blot, 48 hour co-treatment samples for HCT-116 and 72 hours co-treatment samples for HT-29 were used here.

Example 7: miR-3132 Induces Type I Interferon Signaling to Mediate TRAIL Upregulation in Cancer Cells Having confirmed the role of TRAIL in miR-3132 induced apoptosis, the upstream mechanism of TRAIL induction was investigated. For this, bioinformatics analyses, IPA, GSEA and GO (ingenuity pathway analysis, Gene set enrichment analysis and gene ontology respectively) were performed. IPA analysis of all 296 altered genes indicated that the top pathways overlapped with type-I interferon signaling, death receptor signaling, Toll-like receptor signaling and different immune pathways linked to TLRs and IFN response in cells. The top 20 of these pathways and altered genes are listed in FIG. 7, Panel A. Signaling in each of the top four (Type-I interferon signaling, death receptor signaling, Toll-like receptor signaling and different immune pathways) and effector genes altered in the microarray was examined. Of note, interferon signaling was either IFNα/β, mainly indicating a Type I IFN signaling response. When all four pathways in the gene network are linked, all three major pathways, TLR signaling, IFN response, and TRAIL signaling, are observed to be interconnected with a number of overlapping genes (data not shown).

IPA upstream functional analysis was also performed to predict transcriptional regulators from differentially expressed genes post miR-3132 transfection. This analysis indicated a number of Interferon Response Factors (IRFs), both downstream (STAT1, IRF9, STAT2) and upstream (IRF3 for example) of Interferon Type I signaling were activated. Death receptor signaling with TRAIL/Apo2L is an important upstream gene that was up-regulated. Activation of IRF by cytosolic pattern recognition receptors, indicated upregulation of Stat1, Stat2, and IRF9 via type I interferon signaling. Toll-like receptor signaling indicated TLR6 and downstream JAK signaling as key upstream regulators. FIG. 8, shows the list of top activated transcriptional regulators associated with IFN response and the corresponding genes from the microarray altered. Overlap p-values indicate the significant overlap between the genes changed in microarray and known targets regulated by the listed transcriptional regulators. Stat 1, Stat 2 and IRF9 are the key genes that lead to activation of TRAIL. Interferon signaling and TLR6 signaling are the key upstream factors upregulating Stat 1.

Figure 7:
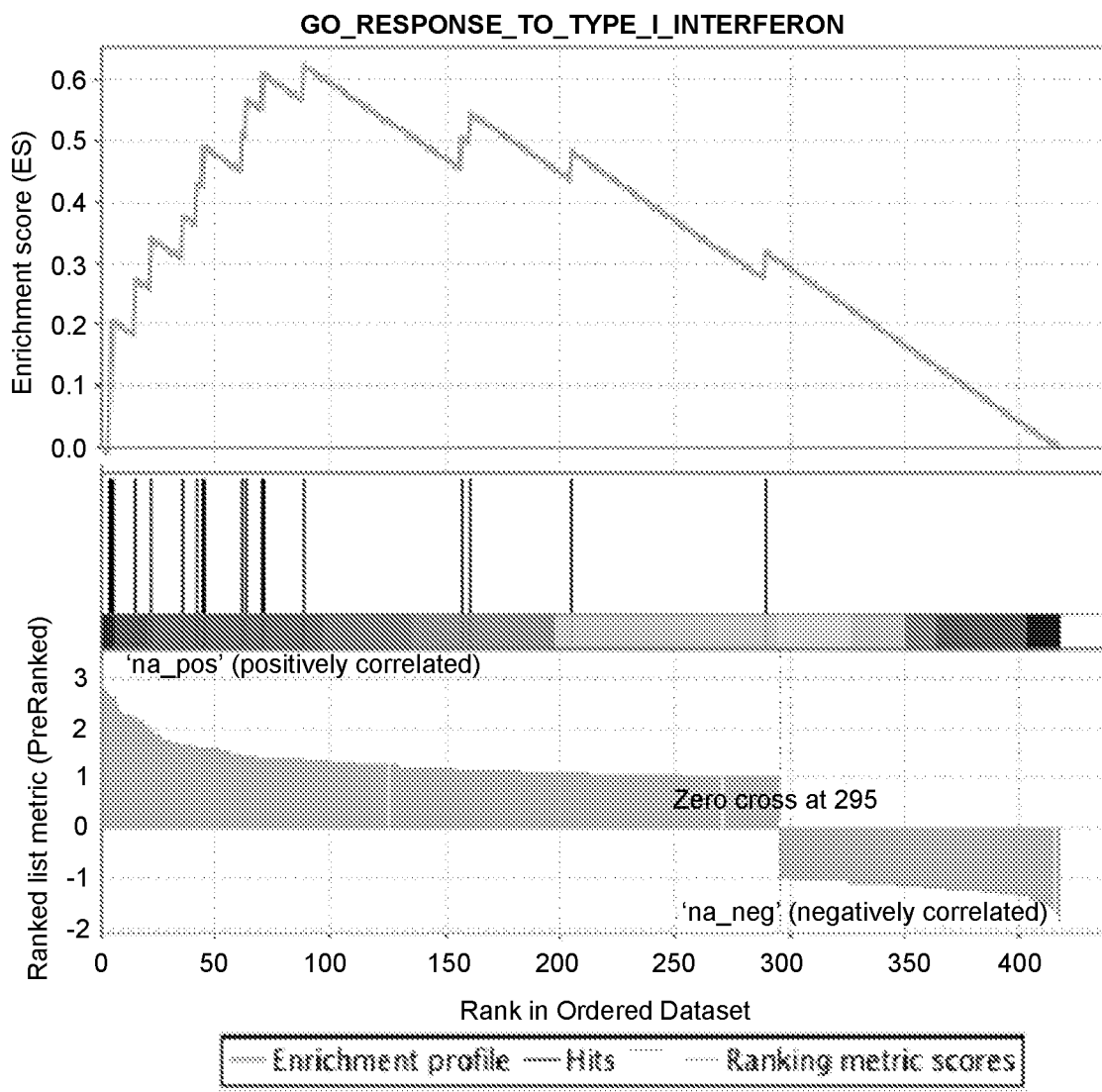
FIG. 7 (Panels A, B, and C) shows miR-3132 primarily upregulates Type I Interferon signaling in cancer cells.
Figure 7:
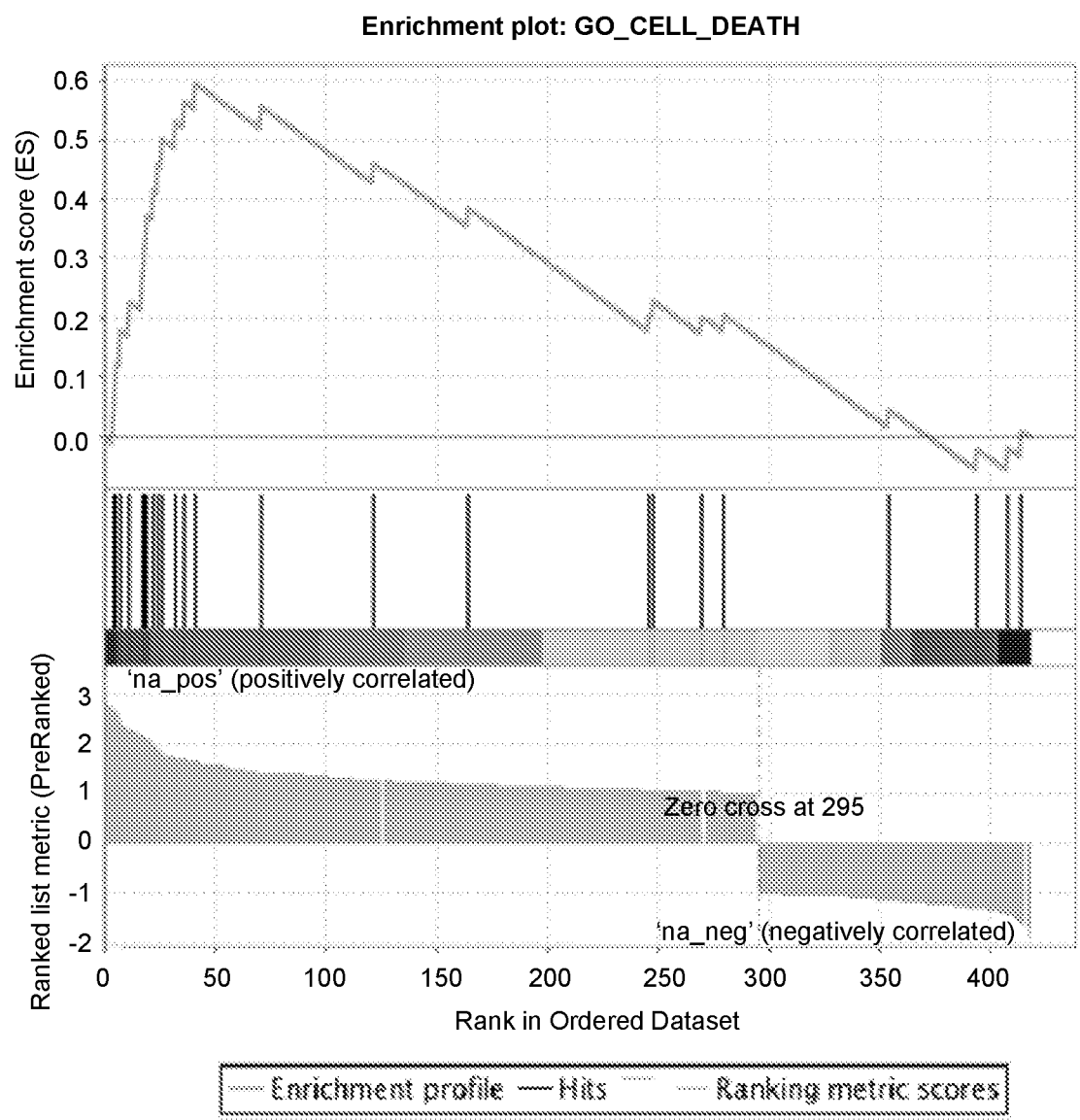
Figure 7:
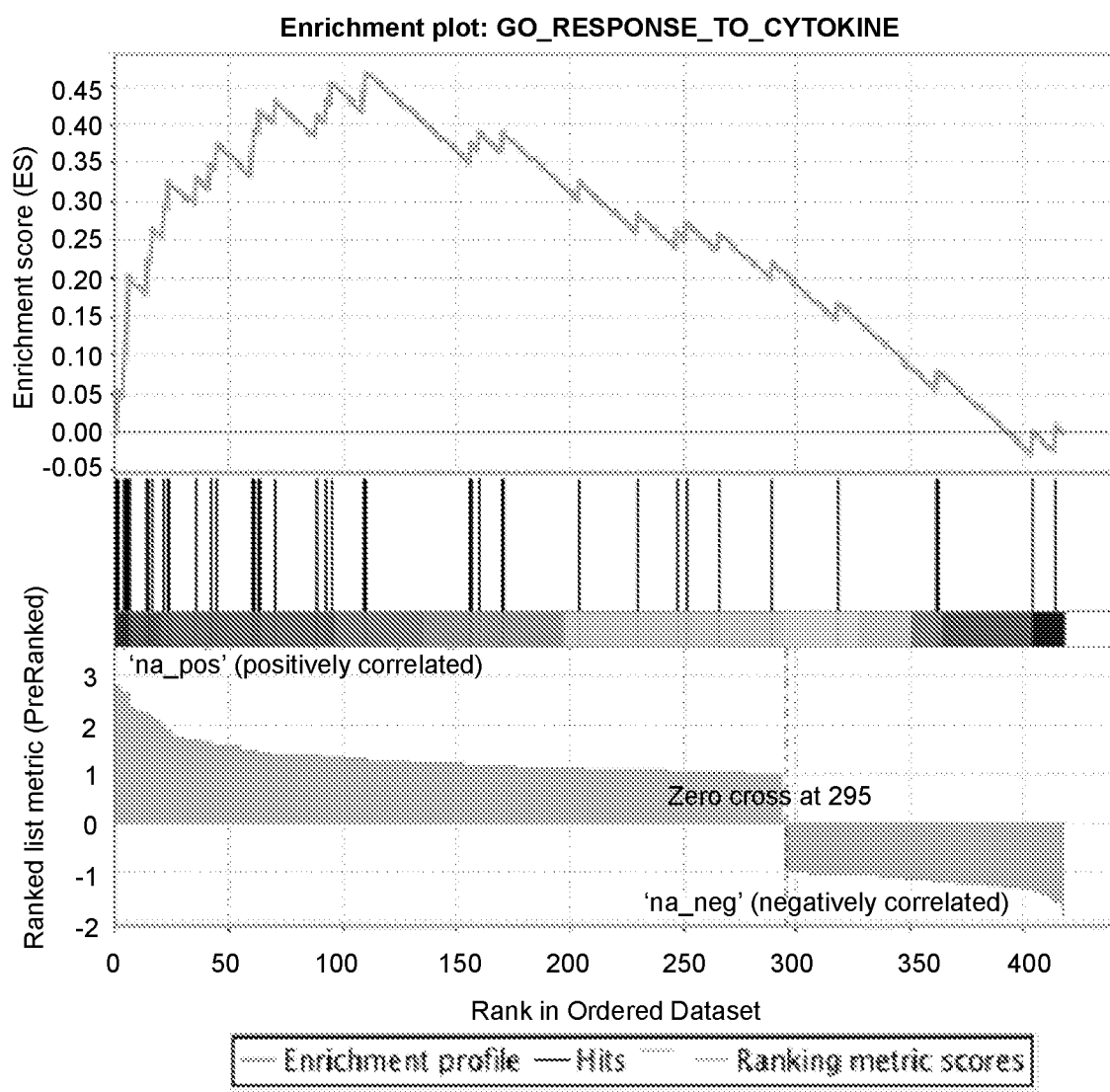
Figure 7:
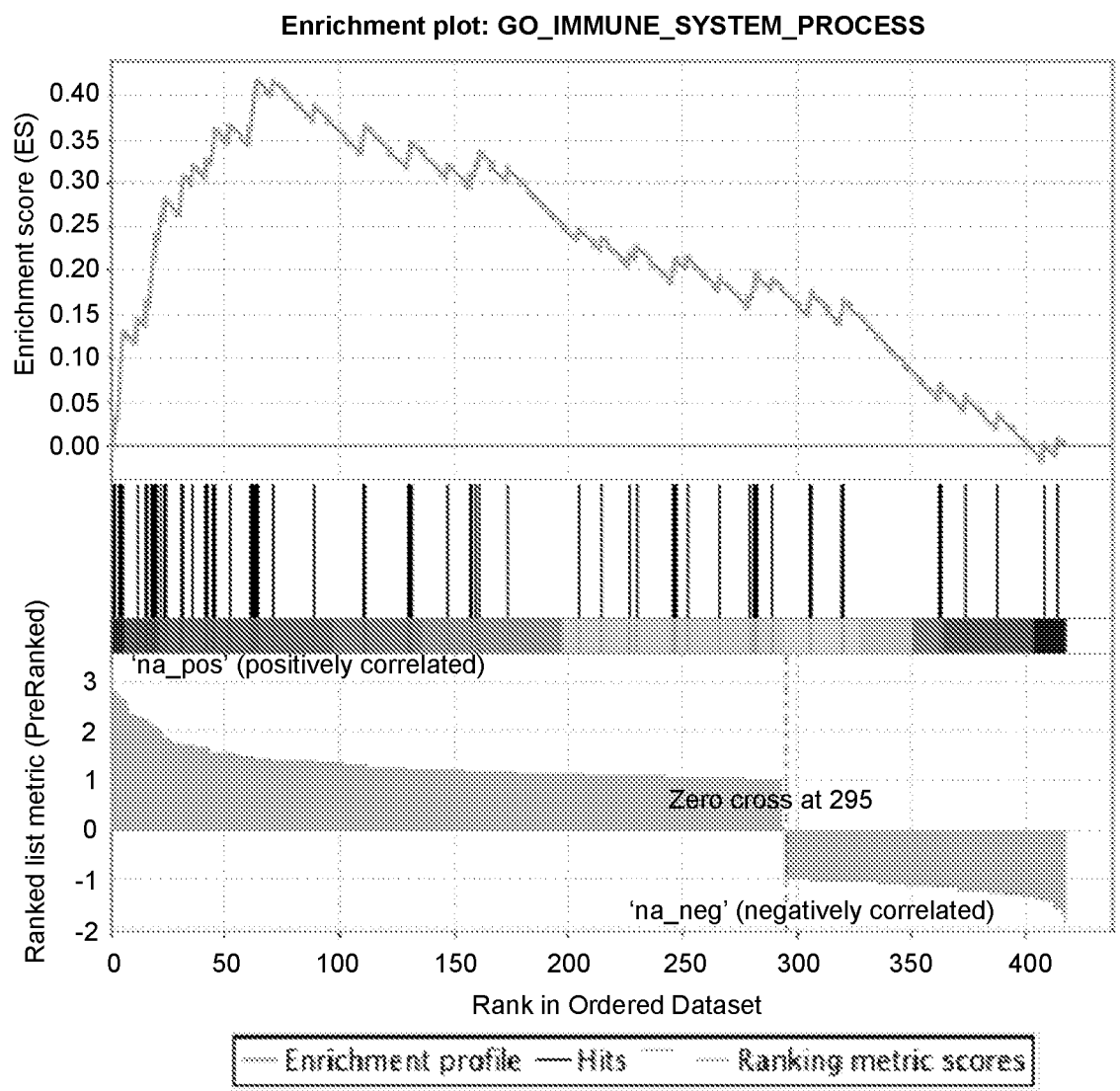
Figure 7:
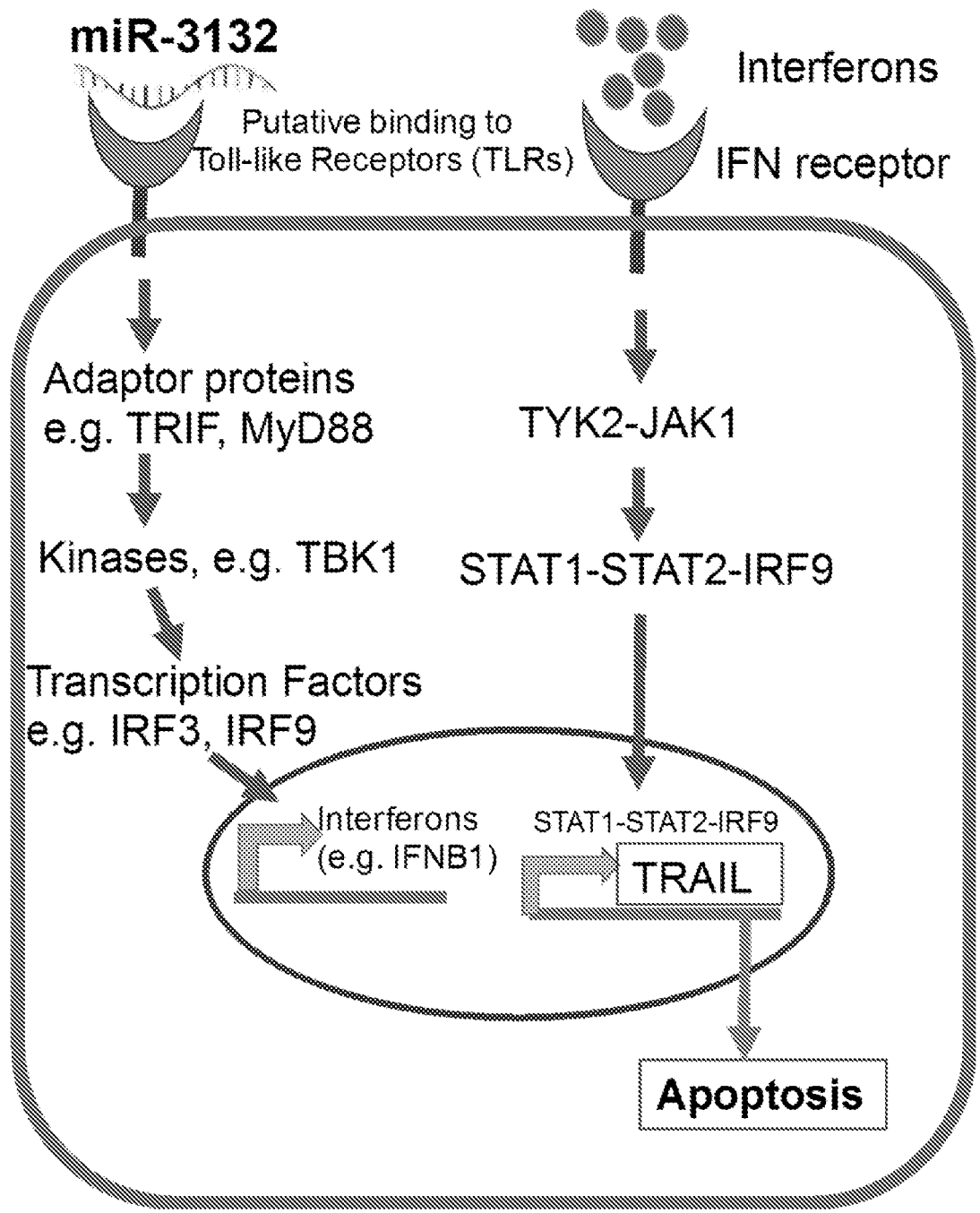

GSEA analysis, a pathway enrichment method, compares the observed gene signature to published and known gene signatures from Molecular Signature Databases (MSigDB). Using this analysis method, gene signatures from Interferon Type I signaling, cell death signaling, immune response and response to cytokines were observed as the key pathways that overlapped with the microarray data. FIG. 9 lists a summary of the GSEA analysis. FIG. 7, Panel B shows the top four GSEA plots indicating the above discussed result. GO (Gene Ontology) analysis supported the above two analyses (data not shown). Here too, an Interferon Type I signaling, response to cytokines and cell death as key biological processes altered in response to miR-3132 were observed. Thus, TLR and IFN signaling are upstream effectors of TRAIL upregulation seen in the dataset (see, FIG. 7, Panel C).

Referring specifically to FIG. 7: (Panel A) List of top 20 pathways altered by miR-3132 were identified with IPA analysis and the genes from microarray changed in the pathways indicated are listed. (Panel B) Four Gene Set Enrichment Analysis (GSEA) plots, specifically plots of Response to Type I Interferon, cell death, response to cytokines and immune system process that the microarray data matched with are shown. (Panel C) Linear and simplified pathway explaining the putative mechanism of TRAIL upregulation of TRAIL and hypothesis of miR-3132 mechanism of action.

Referring specifically to FIG. 8: List of upstream transcriptional regulators activated by miR-3132.

Referring specifically to FIG. 9: GSEA indicating list of gene sets overlapping with gene signature observed with miR-3132 microarray data.

Discussion

The upregulation of TRAIL as an effector molecule is highly regulated and context dependent. In case of immune surveillance, IFN-γ induced expression of TRAIL on NK cells and other immune cells is well established (Allen et al., Cancer Biol. Ther., 2012, 13, 1143-51; and Lim et al., Expert Opin. Ther. Targets, 2015, 19, 1171-85). TRAIL expressing immune cells are known to keep a check on tumor development and enhance efficacy of chemotherapeutics such as 5-fluorouracil (Wang et al., Mol. Oncol., 2015, 9, 1815-24; and Zhu et al., Biomed. Res. Int., 2013, 2013, 293874). TRAIL is also selectively cytotoxic to tumor cells. Hence, activation of TRAIL-dependent death receptor signaling in cancer cells by rhTRAIL or TRAIL receptor agonistic antibodies is an ongoing therapeutic strategy. However, the toxicity associated with rhTRAIL, DR4/DR5 monoclonal antibodies and atrimers has limited their clinical use (Lim et al., Expert Opin. Ther. Targets, 2015, 19, 1171-85). Hence, there is a need for the development of novel non-toxic and highly efficacious TRAIL-based therapies.

Using a HTS strategy, a novel, uncharacterized miRNA (miR-3132) was discovered that could selectively reduce viability in mutant p53-expressing cancer cell lines. As described herein, a detailed characterization of miR-3132 was performed in a broad panel of cancer cell lines including CRC, breast, and NSCLC cells. Short-term and long-term proliferation did not show any significant difference in efficacy of miR-3132 by p53 status. Nevertheless, the broad therapeutic index compared to normal cell lines made it an interesting candidate for development.

miR-3132 engaged the extrinsic pathway of apoptosis in at least ten of the thirteen cell lines tested (4 $p53^{+/+}$ cell lines and 9 p53 mutant cell lines). Interestingly, miR-3132 induced surface TRAIL is observed to be required for induction of apoptosis in all cell lines tested. The present disclosure is the first to report an miRNA-mediated TRAIL upregulation in cancer cell lines. miRNAs normally inhibit protein synthesis by binding to the 3'-UTR regions of mRNAs. Therefore, TRAIL induction may be a consequence of miR-3132 inhibiting synthesis of a TRAIL repressor proteins. However, surprisingly, microarray analysis indicated a robust induction of Type I interferon signaling and toll-like receptor signaling pathways. Both type I IFN and TLR signaling are well characterized and context-dependent upregulators of TRAIL. Transcription factors Stat1, Stat2, IRF9, IFNs (α, β, ε) and upstream TLR signaling via TLR6, IRF3 were seen to be upregulated in miR-3132 microarray data. There may be miR-specific binding of miR-3132 to toll-like receptors (putatively TLR6) which induces production of Type I interferons. These interferons further up-regulate TRAIL through the Stat1-Stat2-IRF9 transcription complex.

In summary, miR-3132 may be a novel TRAIL-inducing regulatory mechanism and candidate therapeutic as an alternative to existing TRAIL based therapies.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating a subject having cancer, the method comprising:
measuring the amount of miR-3132 in a cancer cell from the subject; and
administering a miR-3132 nucleic acid molecule comprising GGUGGGAUGGGUAGA GAAGGAGCUCAGAGGACGGUGCGCCUUGUUUCCCUUGAGCCCUCCCUCUCUCAUC CCACC (SEQ ID NO:1) or UGGGUAGAGAAGGAGCUCAGAGGA (SEQ ID NO:2) to the subject, wherein the amount of miR-3132 in the cancer cell from the subject is lower than a threshold amount of miR-3132.

2. The method according to claim 1, wherein the cancer cell has a mutated p53.

3. The method according to claim 1, wherein the subject is sensitive to a pharmaceutical agent that upregulates TNF-related apoptosis-inducing ligand (TRAIL) or activates TRAIL signaling pathway.

4. The method according to claim 3, wherein the pharmaceutical agent is rhTRAIL, PEG-TRAIL, His-TRAIL, Flag-TRAIL, TRA-8, AMG-655, TIC1, TIC2, TIC4, TIC5, TIC6, TIC7, TIC78 TIC9, TIC10 (ONC201), apomab, mapatumumab, or lexatumumab.

5. The method according to claim 1, wherein the cancer is colorectal cancer, ovarian cancer, breast cancer, lung cancer, or melanoma.

6. The method according to claim 1, the method further comprising administering a pharmaceutical agent that upregulates TNF-related apoptosis-inducing ligand (TRAIL) or activates TRAIL signaling pathway.

7. The method according to claim 6, wherein the pharmaceutical agent is rhTRAIL, PEG-TRAIL, His-TRAIL, Flag-TRAIL, TRA-8, AMG-655, TIC1, TIC2, TIC4, TIC5, TIC6, TIC7, TIC78 TIC9, TIC10 (ONC201), apomab, mapatumumab, or lexatumumab.

8. The method according to claim 1, the method further comprising administering another chemotherapeutic agent to the subject.

9. The method according to claim 8, wherein the another chemotherapeutic agent is tunicamycin, oligomycin, bortezomib, MG132, HDAC inhibitor MS 275, HDAC inhibitor SAHA, HDAC inhibitor LGP1, 5-flurouracil, cisplatin, sorafenib, or flavopiridol.

10. The method according to claim 6, wherein the miR-3132 nucleic acid molecule and the pharmaceutical agent that upregulates TRAIL are present in a single pharmaceutical composition.

11. The method according to claim 6, wherein the miR-3132 nucleic acid molecule and the pharmaceutical agent that upregulates TRAIL are present in separate pharmaceutical compositions.

* * * * *